United States Patent [19]
Pissiotas et al.

[11] Patent Number: 5,817,602
[45] Date of Patent: Oct. 6, 1998

[54] HERBICIDAL THIADIAZABICYCLODECANES

[75] Inventors: Georg Pissiotas, Lörrach, Germany; Hans Moser, Magden; Hans-Georg Brunner, Lausen, both of Switzerland

[73] Assignee: Novartis Corporation, Summit, N.J.

[21] Appl. No.: 569,071

[22] PCT Filed: Jun. 10, 1994

[86] PCT No.: PCT/EP94/01893

§ 371 Date: Dec. 21, 1995

§ 102(e) Date: Dec. 21, 1995

[87] PCT Pub. No.: WO95/00521

PCT Pub. Date: Jan. 5, 1995

[30] Foreign Application Priority Data

Jun. 23, 1993 [CH] Switzerland ............... 1888/93

[51] Int. Cl.$^6$ ............ C07D 513/04; C07D 417/12; A01N 43/90
[52] U.S. Cl. ............ 504/218; 504/196; 504/219; 540/455; 540/491; 540/487; 540/542; 540/568
[58] Field of Search ............ 540/553, 568, 540/455, 491, 487, 542; 504/218, 219, 196

[56] References Cited

U.S. PATENT DOCUMENTS

| 4,684,397 | 8/1987 | Nagano et al. | 71/96 |
| 4,801,408 | 1/1989 | Nagano et al. | 260/508 |

FOREIGN PATENT DOCUMENTS

| 0238711 | 9/1987 | European Pat. Off. . |
| 0273417 | 7/1988 | European Pat. Off. . |
| 0304920 | 3/1989 | European Pat. Off. . |

OTHER PUBLICATIONS

Yamaguchi et al, Chemical Abstracts, vol. 120, entry 2802 (1994).
STN printout of Compounds from Chemical Abstract 120:2802h (1993) for JP 5–213,970.
J. Org. Chem., vol. 46, No. 2, pp. 442–446, Overberger et al., (1981).
Chem. Abst. 86:29859y, p. 375, Wakabayashi et al. (1977).
Chem. Abst. 120:2802h, pp. 333–334, Yamaguchi et al. (1994).

Primary Examiner—John M. Ford
Attorney, Agent, or Firm—William A. Teoli, Jr.

[57] ABSTRACT

Thiadiazabicyclodecanes of formula (I) wherein, Z is oxygen or sulfur; R is an optional substituent and W is an optionally condensed or substituted phenyl radical and the salts, complexes and stereisomers thereof, have good selective pre- and post-emergence herbicidal properties.

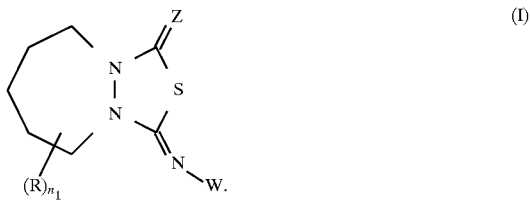

19 Claims, No Drawings

HERBICIDAL THIADIAZABICYCLODECANES

Herbicidal thiadiazabicyclodecanes

The present invention relates to novel, herbicidally active thiadiazabicyclodecanes, to processes for the preparation thereof, to compositions comprising those compounds as active ingredients, and to the use thereof in controlling weeds, especially selectively in crops of useful plants, such as cereals, maize, soybeans, rape, rice and cotton.

Thiadiazabicyclo derivatives having herbicidal activity are already known. Such compounds are disclosed, for example, in EP-A-0 238 711, EP-A-0 304 920, U.S. Pat. No. 4,885,023, U.S. Pat. No. 4,684,397, U.S. Pat. No. 4,801,408 and JP-A-05 213 970.

Novel thiadiazabicyclodecanes having selective herbicidal activity have now been found.

The thiadiazabicyclodecanes according to the invention correspond to formula I

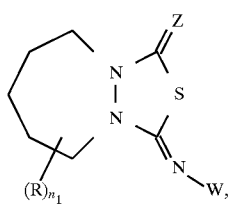

(I)

wherein

Z is oxygen or sulfur;

R is $C_1$–$C_6$alkyl, $C_3$–$C_6$cycloalkyl, $C_1$–$C_6$haloalkyl, $C_3$–$C_6$alkenyl, $C_3$–$C_6$alkynyl, $C_3$–$C_6$haloalkenyl, $C_3$–$C_6$haloalkynyl, phenyl that is unsubstituted or substituted by $C_1$–$C_4$alkyl, $C_1$–$C_4$alkoxy, $C_1$–$C_4$haloalkyl or by halogen, or is benzyl that is unsubstituted or substituted by $C_1$–$C_4$alkyl, $C_1$–$C_4$alkoxy, $C_1$–$C_4$haloalkyl or by halogen, it being possible for the unsubstituted or substituted phenyl and benzyl groups each to occur only once;

W is a group of formula $W_1$ to $W_{10}$

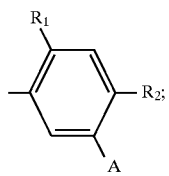

($W_1$)

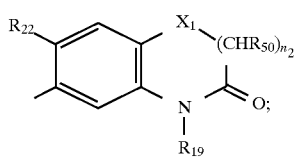

($W_2$)

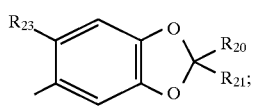

($W_3$)

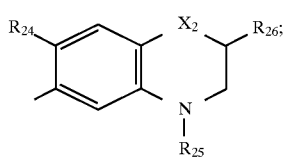

($W_4$)

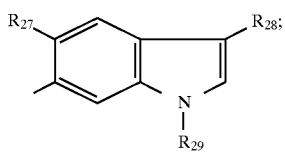

($W_5$)

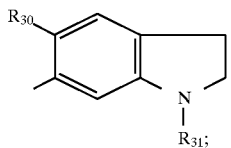

($W_6$)

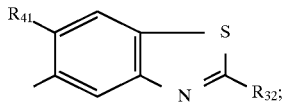

($W_7$)

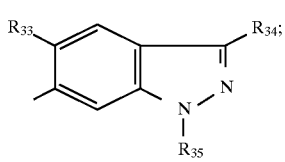

($W_8$)

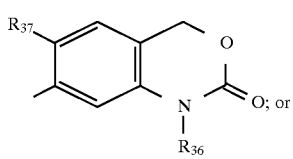

($W_9$)

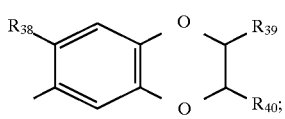

($W_{10}$)

$R_1$, $R_{22}$, $R_{23}$, $R_{24}$, $R_{27}$, $R_{30}$, $R_{33}$, $R_{37}$, $R_{38}$ and $R_{41}$ are each independently of the others hydrogen or halogen;

$R_2$ is cyano, nitro, halogen, $C_1$–$C_4$alkyl, $C_1$–$C_4$haloalkoxy or $C_1$–$C_4$haloalkyl;

A is hydrogen, cyano, nitro, —$COR_3$, —$X_3R_4$,

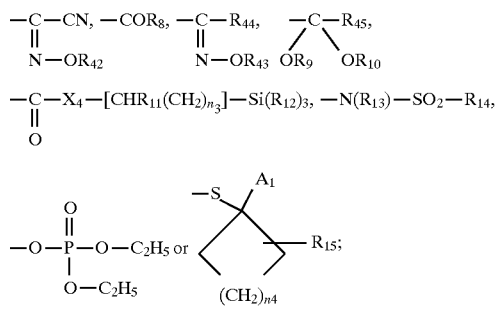

$A_1$ is cyano or —$COR_{16}$;

$R_3$ is halogen, —$X_4$—$R_5$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_3$- or $C_4$-alkenylamino, diallylamino, -N-pyrrolidino, -N-piperidino, -N-morpholino, -N-thiomorpholino, -N-piperazino, —O—N=C($CH_3$)—$CH_3$ or —O—$CH_2$—$CH_2$—O—N=C($CH_3$)—$CH_3$;

$R_4$, $R_{42}$ and $R_{43}$ are hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, $C_1$–$C_8$haloalkyl, $C_2$–$C_8$alkenyl, $C_2$–$C_8$-haloalkenyl, $C_3$–$C_8$alkynyl, $C_3$–$C_7$cycloalkyl, oxetan-3-yl, halo-$C_3$–$C_7$cycloalkyl, $C_1$–$C_8$alkylcarbonyl, allylcarbonyl, $C_3$–$C_7$cycloalkylcarbonyl, benzoyl that is unsubstituted or substituted at the phenyl ring by up to three identical or different substituents selected from halogen, $C_1$–$C_4$alkyl, $C_1$–$C_4$haloalkyl, $C_1$–$C_4$haloalkoxy and $C_1$–$C_4$alkoxy; $C_1$–$C_4$alkyl substituted by cyano, nitro, carboxy, $C_1$–$C_8$alkylthio-$C_1$–$C_8$alkoxycarbonyl, phenyl, halophenyl, $C_1$–$C_4$alkylphenyl, $C_1$–$C_4$alkoxyphenyl, $C_1$–$C_4$haloalkylphenyl, $C_1$–$C_4$haloalkoxyphenyl, $C_1$–$C_6$alkoxycarbonyl, $C_1$–$C_4$-alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$-$C_8$alkynylthiocarbonyl, carbamoyl, $C_1$–$C_4$alkylaminocarbonyl, di-$C_1$–$C_4$alkylaminocarbonyl; phenylaminocarbonyl that is unsubstituted or substituted at the phenyl by up to three identical or different substituents selected from halogen, $C_1$–$C_4$alkyl, $C_1$–$C_4$haloalkyl, $C_1$–$C_4$-haloalkoxy and $C_1$–$C_4$alkoxy or by one substituent selected from cyano and nitro; dioxolan-2-yl that is unsubstituted or substituted by one or two $C_1$–$C_4$alkyl radicals; or dioxanyl that is unsubstituted or substituted by one or two $C_1$–$C_4$alkyl radicals;

$R_5$ is hydrogen, $C_1$–$C_{10}$alkyl, $C_1$–$C_4$alkoxy-$C_1$–$C_4$alkyl, $C_2$–$C_8$haloalkyl, $C_1$–$C_{10}$alkyl-thio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, $C_3$–$C_8$haloalkenyl, $C_3$–$C_8$alkynyl, $C_3$–$C_7$cycloalkyl, oxetan-3-yl, $C_3$–$C_7$cycloalkyl-$C_1$–$C_4$alkyl, halo-$C_3$–$C_7$cycloalkyl, or is benzyl that is unsubstituted or substituted at the phenyl ring by up to three identical or different substituents selected from halogen, $C_1$–$C_4$alkyl, $C_1$–$C_4$haloalkyl, $C_1$–$C_4$haloalkoxy and $C_1$–$C_4$alkoxy; an alkali metal, alkaline earth metal or ammonium ion; or a group —[CHR$_6$(CH$_2$)$_{n5}$]—COOR$_7$;

$R_{20}$ and $R_{21}$ are each independently of the other hydrogen, $C_1$–$C_4$alkyl or fluorine;

$R_6$, $R_{26}$, $R_{28}$, $R_{32}$, $R_{34}$, $R_{39}$, $R_{40}$, $R_{46}$, $R_{47}$, $R_{49}$, $R_{50}$ and $R_{51}$ are each independently of the others hydrogen or $C_1$–$C_4$alkyl;

$R_7$ and $R_{48}$ are each independently of the other hydrogen, $C_1$–$C_6$alkyl, $C_3$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

$R_8$ is hydrogen or $C_1$–$C_4$alkyl;

$R_{44}$ and $R_{45}$ are each independently of the other hydrogen, $C_1$–$C_4$alkyl, $C_1$–$C_4$haloalkyl or $C_1$–$C_4$alkoxy-$C_1$–$C_4$alkyl;

$R_9$ and $R_{10}$ are each independently of the other $C_1$–$C_4$alkyl, $C_2$–$C_4$haloalkyl or $C_2$–$C_8$-alkoxyalkyl; or $R_9$ and $R_{10}$ together are an ethano, a propano or a cyclohexane-1,2-diyl bridge, it being possible for those groups to be either unsubstituted or substituted by one or two radicals from the group $C_1$–$C_4$alkyl, $C_1$–$C_4$haloalkyl and $C_1$–$C_4$hydroxyalkyl;

$R_{11}$ is hydrogen, $C_1$–$C_5$alkyl or $C_3$–$C_7$alkenyl;

$R_{12}$ is $C_1$–$C_8$alkyl;

$R_{13}$ is hydrogen, $C_1$–$C_5$alkyl, benzyl, $C_1$–$C_4$haloalkyl, $C_3$–$C_8$alkenyl or $C_3$–$C_8$alkynyl;

$R_{14}$ is $C_1$–$C_6$alkyl, $C_1$–$C_5$haloalkyl or di-$C_1$–$C_4$alkylamino;

$R_{15}$ is hydrogen, fluorine, chlorine, bromine, $C_1$–$C_4$alkyl or trifluoromethyl;

$R_{16}$ is chlorine, -X$_5$-R$_{17}$, amino, $C_1$–$C_4$alkylamino, di-$C_1$–$C_4$alkylamino, $C_2$–$C_4$haloalkylamino, di-$C_2$-$C_4$haloalkylamino, $C_1$–$C_4$alkoxyalkylamino, di-$C_1$–$C_4$alkoxyalkylamino, $C_3$–$C_4$alkenylamino, diallylamino, —N-pyrrolidino, —N-piperidino, —N-morpholino, —N-thiomorpholino, —N-piperazino, or is a group —O—N=C(CH$_3$)—CH$_3$, —O—CH$_2$—CH$_2$—O—N=C(CH$_3$)—CH$_3$ or —N(OR$_{46}$)—R$_6$;

$R_{17}$ is hydrogen, $C_1$–$C_{10}$alkyl, $C_1$–$C_4$alkoxy-$C_1$–$C_4$alkyl, $C_2$–$C_8$haloalkyl, $C_1$–$C_{10}$alkyl-thio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, $C_3$–$C_8$haloalkenyl, $C_3$–$C_8$alkynyl, $C_3$–$C_7$cycloalkyl, $C_3$–$C_7$cycloalkyl $C_1$–$C_4$alkyl, halo-$C_3$–$C_7$cycloalkyl, or is benzyl that is unsubstituted or substituted at the phenyl ring by up to three identical or different substituents selected from halogen, $C_1$–$C_4$-alkyl, $C_1$–$C_4$haloalkyl, $C_1$–$C_4$haloalkoxy and $C_1$–$C_4$alkoxy; an alkali metal, alkaline earth metal or ammonium ion, or a group —[CHR$_{47}$—(CH$_2$)$_m$]—COOR$_{48}$ or —[CHR$_{49}$—(CH$_2$)$_t$—Si(R$_{18}$)$_3$];

m is 0, 1, 2, 3 or 4;

t is 0, 1, 2, 3 or 4;

$R_{18}$ is $C_1$–$C_4$alkyl;

$R_{19}$ is hydrogen, $C_1$–$C_6$alkyl, $C_2$–$C_4$alkenyl or $C_2$–$C_6$alkynyl; halo-substituted $C_1$–$C_6$-alkyl, $C_2$–$C_4$alkenyl or $C_3$–$C_6$alkynyl; $C_1$–$C_4$alkoxy-$C_1$–$C_4$alkyl, $C_1$–$C_4$alkoxy-$C_1$–$C_2$-alkoxy-$C_1$–$C_2$alkyl, 1-phenylpropen-3-yl, cyano- or $C_3$–$C_6$cycloalkyl-substituted $C_1$–$C_6$alkyl; carboxy-$C_1$–$C_4$alkyl, $C_1$C$_6$alkoxycarbonyl-$C_1$–$C_4$alkyl, $C_2$–$C_6$haloalkoxycarbonyl-$C_1$–$C_4$alkyl, $C_1$–$C_4$alkoxy-$C_1$–$C_2$alkoxycarbonyl-$C_1$–$C_4$alkyl, $C_1$–$C_6$alkoxycarbonyl-$C_1$–$C_2$alkoxycarbonyl-$C_1$–$C_4$alkyl, $C_3$–$C_6$cycloalkyl-$C_1$–$C_2$alkoxycarbonyl-$C_1$–$C_4$alkyl, $C_1$–$C_5$alkylaminocarbonyl-$C_1$–$C_4$alkyl, di-$C_1$—$C_4$alkylamino-$C_1$–$C_4$alkyl, di-$C_1$–$C_5$alkylaminocarbonyl-$C_1$–$C_4$alkyl, $C_3$–$C_6$cycloalkyl, $C_1$–$C_4$alkylthio-$C_1$–$C_4$alkyl, benzyl or halo-substituted benzyl, $C_1$–$C_4$alkylsulfonyl, $C_3$–$C_6$alkenyloxy-$C_1$–$C_4$alkyl, $C_1$–$C_4$alkoxycarbonyl, $C_1$–$C_8$alkylcarbonyl,

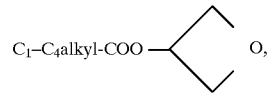

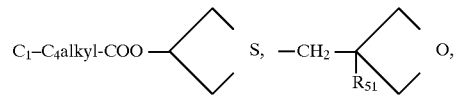

$C_1$–$C_4$alkylthiocarbonyl-$C_1$–$C_4$alkyl, or a group —[CHR$_{47}$—(CH$_2$)$_m$]COX$_6$—CHR$_{47}$—(CH$_2$)$_m$—COOR$_{48}$;

$R_{25}$, $R_{29}$, $R_{31}$, $R_{35}$ and $R_{36}$ are each independently of the others hydrogen, $C_1$–$C_4$alkyl, $C_1$–$C_6$haloalkyl, $C_3$–$C_8$alkenyl, $C_3$–$C_8$haloalkenyl, $C_3$–$C_8$alkynyl, $C_1$–$C_4$alkoxy-$C_1$–$C_8$alkyl, cyano-$C_1$–$C_4$alkyl, $C_1$–$C_8$alkoxycarbonyl-$C_1$–$C_4$alkyl, $C_3$–$C_7$cycloalkyl, $C_3$–$C_7$cycloalkyl-$C_1$–$C_4$alkyl, benzyl, $C_1$–$C_4$alkyl substituted by —N-morpholino, —N-thiomorpholino or by —N-piperazino, di-$C_1$–$C_4$alkylamino-$C_1$–$C_4$alkyl, $C_1$–$C_4$-alkylaminocarbonyl-$C_1$–$C_4$alkyl, di-$C_1$–$C_4$alkylaminocarbonyl-$C_1$–$C_4$alkyl, $C_1$–$C_4$-alkoxycarbonyl or $C_1$–$C_4$alkylcarbonyl;

$X_1$, $X_2$, $X_3$, $X_4$, $X_5$ and $X_6$ are each independently of the others oxygen or sulfur; and $n_1$, $n_2$, $n_3$, $n_4$ and $n_5$ are each independently of the others 0, 1, 2, 3 or 4;

and the salts, complexes and stereoisomers thereof.

In the above definitions, halogen is to be understood as being fluorine, chlorine, bromine and iodine, preferably fluorine, chlorine and bromine.

Suitable alkyl groups are straight-chained or branched alkyl groups, for example methyl, ethyl, n-propyl, isopropyl, n-butyl, isobutyl, sec-butyl, tert-butyl, and the various isomeric pentyl, hexyl, heptyl, octyl, nonyl and decyl radicals.

Suitable as haloalkyl are alkyl groups mono- or polysubstituted, especially mono- to tri-substituted, by halogen, halogen being individually bromine or iodine and especially fluorine or chlorine, for example fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably difluorochloromethyl, trifluoromethyl, dichlorofluoromethyl and trichloromethyl.

Alkoxy is, for example, methoxy, ethoxy, n-propoxy, isopropoxy, n-butoxy, isobutoxy, sec-butoxy and tert-butoxy; preferably methoxy, ethoxy and isopropoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, trifluoromethoxy and 2-chloroethoxy.

Alkylthio is, for example, methylthio, ethylthio, n-propylthio, isopropylthio, n-butylthio, isobutylthio, sec-butylthio, tert-butylthio or isomeric pentylthio, preferably methylthio and ethylthio.

Alkenyl is to be understood as being straight-chained or branched alkenyl, such as vinyl, allyl, methallyl, 1-methylvinyl, but-2-en-1-yl, pentenyl, 2-hexenyl or 3-heptenyl; the same applies also to the alkenyl moiety of alkenyloxy, alkenylthio and alkenylamino groups. Preference is given to alkenyl radicals having a chain length of from 2 to 4 carbon atoms.

The alkynyl radicals in the definitions of the substituents may be straight-chained or branched, such as ethynyl, propargyl, 3-butynyl, 1-methylpropargyl, 1-pentynyl or 2-hexynyl; the same applies also to the alkynyl moiety of alkynyloxy and alkynylthio groups. Preference is given to ethynyl, propargyl and 1-methylpropargyl.

Cycloalkyl is, for example, cyclopropyl, dimethylcyclopropyl, cyclobutyl, cyclopentyl, methylcyclopentyl, cyclohexyl or cycloheptyl, but preferably cyclopropyl, cyclopentyl and cyclohexyl.

Alkoxycarbonyl is, for example, methoxycarbonyl, ethoxycarbonyl, n-propoxycarbonyl, isopropoxycarbonyl or n-butoxycarbonyl, preferably methoxycarbonyl and ethoxycarbonyl.

Alkoxyalkyl is, for example, methoxymethyl, ethoxymethyl, propoxymethyl, methoxyethyl, ethoxyethyl, propoxyethyl, methoxypropyl, ethoxypropyl or propoxypropyl.

Alkylthioalkyl is, for example, methylthiomethyl, ethylthiomethyl, methylthioethyl, ethylthioethyl or isopropylthioethyl.

Alkylamino is, for example, methylamino, ethylamino and isomeric propyl- and butylamino.

Cyanoalkyl is, for example, cyanomethyl, cyanoethyl or cyanopropyl.

Halocycloalkyl is, for example, 2,2-dichlorocyclopropyl or pentachlorocyclohexyl.

Alkylsulfonyl is, for example, methylsulfonyl, ethylsulfonyl, propylsulfonyl or butylsulfonyl, preferably methyl- and ethyl-sulfonyl.

Phenyl, also as part of a substituent such as phenoxy, phenylthio, phenoxycarbonyl, phenylaminocarbonyl, benzyl or benzoyl, may generally be unsubstituted or substituted. In the latter case, the substituents may be in the ortho-, meta- and/or para-position. Preferred substituent positions are the ortho- and para-positions to the ring-linkage position. Preferred substituents are halogen atoms.

The substituents in combined definitions, such as alkoxyalkoxycarbonylalkyl, alkylthioalkoxycarbonyl, haloalkoxycarbonylalkyl, alkoxyalkoxyalkyl, cycloalkylalkyl, cycloalkylalkoxycarbonylalkyl and alkoxyalkylamino, may have the same definitions as those above.

The salts of compounds of formula I having acidic hydrogen, especially of derivatives having carboxylic acid groups (A=—C(O)—$X_4R_5$ wherein $X_4$ is oxygen and $R_5$ is hydrogen), are, for example, alkali metal salts, such as sodium and potassium salts; alkaline earth metal salts, such as calcium and magnesium salts; ammonium salts, i.e. unsubstituted ammonium salts and mono- or poly-substituted ammonium salts, such as tri-ethylammonium and methylammonium salts; or salts with other organic bases.

Examples of amines suitable for salt formation are primary, secondary and tertiary aliphatic and aromatic amines, such as methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methylhexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylenediamine, diethanolamine, trimethylamine, triethylamine, tri-n-propylamine, tri-isopropylamine, tri-n-butylamine, tri-isobutylamine, tri-sec-butylamine, tri-n-amylamine; heterocyclic amines, such as pyridine, quinoline, isoquinoline, morpholine, thiomorpholine, N-methylmorpholine, N-methyl-thiomorpholine, piperidine, pyrrolidine, indoline, quinuclidine and azepine; primary arylamines, such as anilines, methoxyanilines, ethoxyanilines, o,m,p-toluidines, phenylenediamines, benzidines, naphthylamines and o,m,p-chloroanilines.

The fact that at least one asymmetric carbon atom may be present in compounds of formula I, for example in ester and ether derivatives having substituted aliphatic and alicyclic groups, means that the compounds may occur both in the form of optically active individual isomers and in the form of racemic mixtures. In the present invention, compounds of formula I are to be understood as being both the pure optical antipodes and the racemates. If an aliphatic C=C or C=N double bond is present, geometric isomerism may also occur.

Preference is given to compounds of formula I wherein Z is oxygen.

Preference is likewise given to compounds of formula Ia (Ia)

wherein Z, A, R, $R_1$, $R_2$ and $n_1$ are as defined for formula I.

Of those compounds, special preference is given to those wherein A is —$X_3R_4$, —$COR_8$, —$COR_3$, $$-\underset{OR_9}{\overset{|}{C}}\underset{OR_{10}}{\overset{|}{-}}R_{45}, \quad -\underset{N-OR_{42}}{\overset{\|}{C}}-CN, \quad -\underset{N-OR_{43}}{\overset{\|}{C}}-R_{44}$$

or —N($R_{13}$)—$SO_2$—$R_{14}$, wherein $X_3$ is especially sulfur and R4 is $C_1$–$C_4$alkyl substituted by $C_1$–$C_6$alkoxycarbonyl.

In especially preferred compounds of formula Ia, $R_1$ and $R_2$ are halogen; $R_1$ is especially fluorine and $R_2$ is especially chlorine.

The preferred compounds likewise include those of formula Ib (Ib)

wherein Z, R, $R_{19}$, $R_{22}$, $X_1$, $R_{50}$, $n_1$ and $n_2$ are as defined for formula I.

Of those compounds, special preference is given to those wherein $R_{19}$ is $C_1$–$C_4$alkyl, $C_3$- or $C_4$-alkenyl, $C_3$- or $C_4$-haloalkenyl, $C_3$–$C_6$alkynyl, $C_1$–$C_4$-alkoxy-$C_1$–$C_4$alkyl, cyano-$C_1$–$C_4$alkyl, $C_1C_6$alkoxycarbonyl-$C_1$–$C_4$alkyl, $C_3$–$C_6$-cycloalkyl, $C_3$–$C_6$cycloalkyl-$C_1C_4$alkyl, benzyl, di-$C_1$–$C_4$alkylamino-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_1$–$C_4$alkoxycarbonyl or $C_1$–$C_4$alkylcarbonyl.

Of those compounds very special preference is given to those wherein

Z is oxygen;

$R_{19}$ is $C_1$–$C_3$alkyl, $C_1$–$C_3$alkoxycarbonyl-$C_1$- or -$C_2$-alkyl or $C_3$- or $C_4$-alkynyl;

$R_{22}$ is hydrogen or fluorine;

$R_{50}$ is hydrogen; and $n_2$ is 0 or 1.

Especially significant are compounds of formula I wherein $n_1$ is 0 or 1.

Of those, compounds of formula I wherein $n_1$ is 0 are of very special significance.

Very especially preferred individual compounds within the scope of formula I that may be mentioned are:

10-(4-chloro-2-fluoro-5-isopropoxycarbonyl-phenylimino)-9-thia-1,7-diazabicyclo[3.5.0]-decan-8-one; and 10-(4-chloro-2-fluoro-5-methoxycarbonyl-phenylimino)-9-thia-1,7-diazabicyclo[3.5.0]-decan-8-one.

The process according to the invention for the preparation of compounds of formula I (I)

wherein Z, W, R and $n_1$ are as defined for formula I, is carried out analogously to known processes and comprises converting an isothiocyanate of formula II $$S=C=N-W, \qquad (II)$$

wherein W is as defined for formula I, with a compound of formula III (III)

wherein R and $n_1$ are as defined, into a compound of formula IV (IV)

which is then reacted, where appropriate in the presence of a base, with a compound of formula V $$CZCl_2 \qquad (V)$$

wherein Z is oxygen or sulfur.

The reaction of an isothiocyanate of formula II with a compound of formula HI is advantageously carried out in an inert organic solvent at temperatures of from –5° C. to the boiling temperature of the solvent, especially from 0° to +50° C., preferably at room temperature. Examples of suitable solvents for that reaction are toluene, xylenes, ethyl acetate and acetonitile.

The reaction of a compound of formula IV with a compound of formula V is advantageously carried out in an inert organic solvent at low temperatures, preferably at from 0° to +50° C., especially at from 0° to +15° C. Examples of bases suitable for that reaction are pyridine, triethylamine and N,N-dimethylaniline. Suitable solvents are, for example, 1,2-dichloroethane, dichloromethane and toluene.

The starting compounds of formula III wherein R is alkyl and $n_1$ is as defined for formula I that are required for the preparation process according to the invention are either known or can be prepared analogously to processes known from the literature. The preparation of such compounds from 1,5-dibromopentanes and hydrazine is described, for example, in "Archiv der Pharmazie" 295 (7), 526 (1962) and J. Org. Chem. 46, 442 (1981).

Compounds of formula IIIa (dihydrobromide)

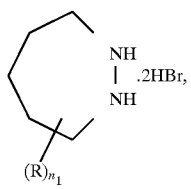
(IIIa)

wherein R and $n_1$ are as defined for formula I, can be prepared in accordance with Reaction scheme 1.

711, EP-A-0 409 025, EP-A-0 373 461, EP-A-0 311 135 and DE-OS-3 724 098.

For the use of the compounds of formula I according to the invention or compositions comprising them there are suitable any of the methods of application customary in agriculture, such as preemergence application, postemergence application and seed dressing, as well as various methods and techniques, such as the controlled release of active ingredient. In that method the compound is applied in solution to mineral granule carriers or polymerised granules (urea/formaldehyde) and dried. Where appropriate, it is also possible to apply a coating (coated granules) which allows the active ingredient to be released in metered amounts over a specific period.

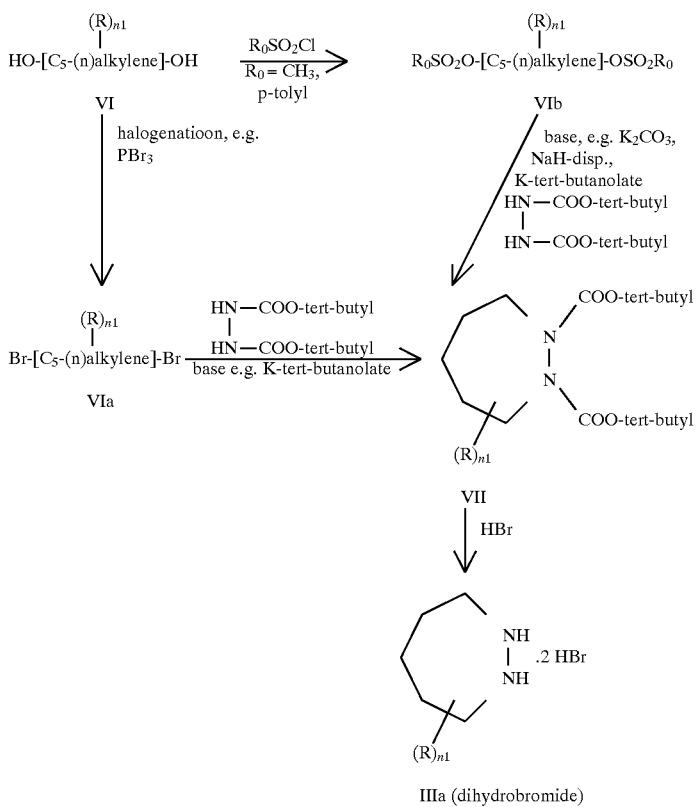

In Reaction scheme 1, formulae VI, VIa and VIb are each an unbranched aliphatic pentane chain having a hydroxy group (VI) or an $R_0SO_2O$ group (VIb) or bromine (VIa) bonded to each of its terminal carbon atoms $C_1$ and $C_5$. The radical R can be linked 0, 1, 2, 3 or 4 times to all of the 5 carbon atoms of the n-pentane chain, where appropriate also geminally.

The intermediates of formulae III and IV wherein R is $C_3$–$C_6$cycloalkyl, $C_1$–$C_6$haloalkyl, $C_3$–$C_6$alkenyl, $C_3$–$C_6$alkynyl, $C_3$–$C_6$haloalkenyl, or $C_3$–$C_6$haloalkynyl, and of formula VI wherein R is $C_1$–$C_6$haloalkyl, $C_3$–$C_6$haloalkenyl or $C_3$–$C_6$haloalkynyl, and $n_1$ is 1, 2, 3 or 4 are novel and have been developed especially for the synthesis of the compounds of formula I. The present invention therefore relates also thereto.

The isothiocyanates of formula II are known or can be prepared analogously to known processes. Such compounds are described, for example, in EP-A-0 304 920, EP-A-0 238

The compounds of formula I can be used in unmodified form, i.e. as obtained during synthesis, but are preferably formulated in customary manner together with the adjuvants conventionally employed in formulation technology, e.g. into emulsifiable concentrates, directly sprayable or dilutable solutions, dilute emulsions, wettable powders, soluble powders, dusts, granules and microcapsules. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compound (active ingredient) of formula I or at least one compound of formula I and, where appropriate, one or more solid or liquid adjuvants, are prepared in known manner, e.g. by homogeneously mixing and/or grinding the active ingredients with the adjuvants, e.g. solvents or solid carriers. Surface-active compounds (surfactants) may additionally be used in the preparation of the formulations.

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons such as paraffins, cyclohexane or tetrahydronaphthalene; alcohols, such as ethanol, propanol or butanol; glycols and their ethers and esters, such as propylene glycol or dipropylene glycol ether, ketones such as cyclohexanone, isophorone or diacetone alcohol, strongly polar solvents such as N-methyl-2-pyrrolidone, dimethyl sulfoxide or water; vegetable oils and their esters, such as rape oil, castor oil or soybean oil; and optionally also silicone oils.

The solid carriers used e.g. for dusts and dispersible powders are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, such as especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil; mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates. The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, for example the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, it being possible for said derivatives to contain 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol polyethoxyethanols, castor oil polyglycol ethers, polypropylenelpolyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, for example stearyltrimethylammonium chloride or benzyldi(2-chloroethyl)ethylammonium bromide.

The surfactants customarily employed in formulation technology, which can also be used in the compositions according to the invention, are described inter alia in the following publications:

"McCutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" (Surfactant Handbook), Carl Hanser Verlag, Munich/Vienna 1981.

The herbicidal compositions usually comprise 0.1 to 99%, preferably 0.1 to 95%, of a compound of formula I, 1 to 99% of a solid or liquid adjuvant, and 0 to 25%, preferably 0.1 to 25%, of a surfactant.

Whereas commercial products are preferably formulated as concentrates, the end user will normally employ dilute formulations.

The compositions may also comprise further ingredients such as stabilisers, e.g. vegetable oils and epoxidised vegetable oils (epoxidised coconut oil, rape oil or soybean oil), antifoams, e.g. silicone oil, preservatives, viscosity regulators, binders and tackifiers, as well as fertlisers or other active ingredients for obtaining special effects. Preferred formulations have especially the following composition (throughout, percentages are by weight)

| Emulsifiable concentrates: | |
|---|---|
| active ingredient: | 1 to 90%, preferably 5 to 50% |
| surfactant: | 5 to 30%, preferably 10 to 20% |
| liquid carrier: | 15 to 94%, preferably 70 to 85% |
| Dusts: | |
| active ingredient: | 0.1 to 50%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |

-continued

| | |
|---|---|
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The compounds of formula I are generally used successfully at rates of application of from 0.001 to 2 kg/ha, especially from 0.005 to 1 kg/ha. The concentration required to achieve the desired effect can be determined by experiment. It is dependent upon the type of action, the stage of development of the crop plant and of the weed, and also upon the application (place, time, method) and, in dependence on those parameters, can vary within wide limits.

When used at relatively low rates of application, the compounds of formula I are distinguished by growth-inhibiting and herbicidal properties that make them outstandingly suitable for use in crops of useful plants, especially in cereals, maize, rape, soybeans, rice and cotton.

Crops are also to be understood as being those which have been rendered tolerant to herbicides or classes of herbicide by conventional methods of breeding or by genetic techniques.

The Examples that follow further illustrate, but do not limit, the invention.

PREPARATION EXAMPLES

Example P1
Preparation of 3-trifluoromethyl-1.5-pentanediol (intermediate)

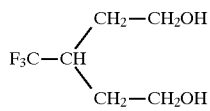

Under a pressure of 150 mm Hg, 136.3 g of 3-trifluoromethylglutaric acid diethyl ester in 1400 ml of ethanol at 150° C. are hydrogenated with hydrogen in the presence of 136.0 g of copper chromite catalyst. When a stoichiometric amount of hydrogen has been absorbed, the catalyst is filtered off and the solution is concentrated in vacuo. The residue is distilled in vacuo to yield 76.9 g of the desired product having a boiling point of 132°–135° C./24 mm Hg.

Example P2
Preparation of 1.5-bismethanesulfonyloxy-3-trifluoromethylpentane (intermediate)

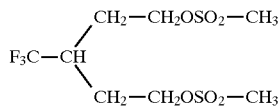

With stirring at 0° C., 63 ml of methylsulfonyl chloride in 40 ml of toluene are added dropwise to a solution of 69.3 g of 3-trifluoromethyl-1,5-pentanediol and 140 ml of triethylamine in 150 ml of toluene. After 12 hours' stirring at room temperature, the solid portions are filtered off and the toluene solution is concentrated in vacuo to give in almost quantitative yield 1,5-bismethanesulfonyloxy-3-trifluoromethylpentane; m.p. 40°–45° C.

Example P3
Preparation of 1,2-dicarboxylic acid di-tert-butyl-5-trifluoromethyl-1,2-diazacycloheptane ( intermediate)

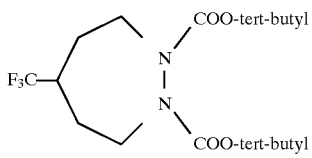

At 0°–5° C., under a nitrogen atmosphere, a solution of 3.5 g of hydrazine-N,N'-dicarboxylic acid di-tert-butyl ester in 50 ml of dimethylformamide is added dropwise to a suspension of 1.2 g of sodium hydride in 60 ml of dimethylformamide. After one hour, 5.1 g of 1,5-bismethanesulfonyloxy-3-trifluoromethylpentane are added thereto at room temperature. The reaction mixture is then stirred for 16 hours at that temperature, then poured onto ice-water and filtered to yield 4.4 g of the desired 1,2-dicarboxylic acid di-tert-butyl-5-trifluoromethyl-1,2-diazacycloheptane having a melting point of 98°–100° C.

Example P4
Preparation of 5-trifluoromethyl-1.2-diazacycloheptane dihydrobromide (intermediate)

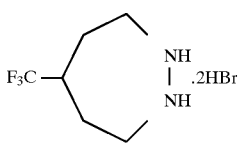

With stirring at room temperature, 6 ml of 33% hydrobromic acid in glacial acetic acid are added dropwise to a solution of 4.3 g of 1,2-dicarboxylic acid di-tert-butyl-5-trifluoromethyl-1,2-diazacycloheptane in 120 ml of diethyl ether. After ½ hour the salt precipitates partially in the form of a white crystalline compound. After the addition of a further 120 ml of diethyl ether the product precipitates completely. The crystalline precipitate is filtered off and the desired product is obtained in a yield of 2.0 g. The very hygroscopic product is dried over phosphorus pentoxide and immediately reacted further.

Example P5
Preparation of 1-[2-chloro-4-fluoro-5-(1-(5-trifluoromethyl)-hexahydro-diazepinyl-thiocarbonylamino]-benzoic acid methyl ester (intermediate)

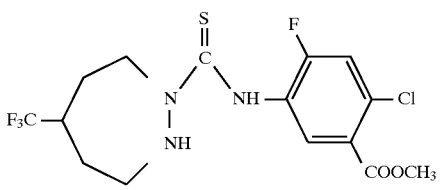

With stirring at 0°–5° C., a solution of 2.2 g of 1-(2-chloro-4-fluoro-5-isothiocyanatobenzoic acid methyl ester in 90 ml of ethylene chloride is added dropwise to a solution of 3.0 g of 5-trifluoromethyl-1,2-diazacycloheptane dihydrobromide in 100 ml of ethanol and 2.7 ml of triethylamine. After three hours' stirring at room temperature, the reaction mixture is taken up in 100 ml of water and 250 ml of ethyl acetate. The organic phase is separated off, dried over sodium sulfate and concentrated in vacuo to yield 3.7 g of the desired intermediate; m.p. 103° C.

Example P6

Preparation of 10-[4-chloro-2-fluoro-5-methoxycarbonyl-phenyliminol]-9-thia-4-trifluoromethyl-1,7-diazabicyclo[5.3.0]decan-8-one

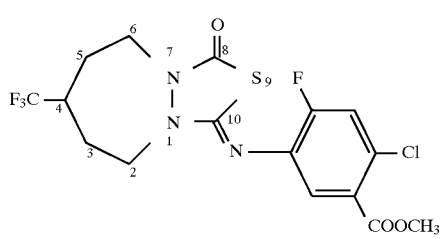

(2.005)

With stirring at 0°–5° C., a solution of 3.7 g of 1-[2-chloro-4fluoro-5-(1-(5-trifluoromethyl)-hexahydrodiazepinyl-thiocarbonylamino]-benzoic acid methyl ester in 100 ml of toluene is added dropwise to a solution of 50 ml of toluene and 7 ml of a 20% solution of phosgene in toluene. The reaction mixture is then stirred for 12 hours at room temperature and then poured onto ice-water. The organic phase is separated off, dried over sodium sulfate and concentrated in vacuo to yield 2.5 g of the desired product having a m.p. of 75° C.

The compounds of formula I listed in the following Tables 1 to 16 are prepared in an analogous manner.

TABLE 1

Compounds of formula Ic:

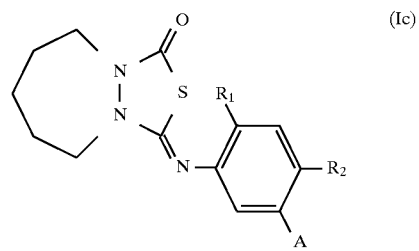

(Ic)

| Comp. No. | $R_1$ | $R_2$ | A | phys. data |
|---|---|---|---|---|
| 1.001 | F | Cl | —H | |
| 1.002 | F | Cl | —CN | |
| 1.003 | F | Cl | —NO$_2$ | |
| 1.004 | F | Cl | —COOH | |
| 1.005 | F | Cl | —COOCH$_3$ | $n_D^{20}$ 1.6069 |
| 1.006 | F | Cl | —COOC$_2$H$_5$ | |
| 1.007 | F | Cl | —COOC$_3$H$_7$ | |
| 1.008 | F | Cl | —COOCH(CH$_3$)$_2$ | $n_D^{19}$ 1.5548 |
| 1.009 | F | Cl | —COOC$_4$H$_9$ | |
| 1.010 | F | Cl | —COOCH—CH$_2$—CH$_3$ \| CH$_3$ | |
| 1.011 | F | Cl | —COOCH$_2$—CH$_2$—CH(CH$_3$)$_2$ | |
| 1.012 | F | Cl | —COOC$_5$H$_{11}$ | |
| 1.013 | F | Cl | —COOCH$_2$—CH$_2$—O—CH$_3$ | |
| 1.014 | F | Cl | —COOCH$_2$—CH$_2$—O—C$_2$H$_5$ | |
| 1.015 | F | Cl | —COOCH(CH$_3$)—CH$_2$—OCH$_3$ | |
| 1.016 | F | Cl | —COOCH$_2$—CH$_2$—S—CH$_3$ | |
| 1.017 | F | Cl | —COOCH(CH$_3$)—CH$_2$—S—CH$_3$ | |

TABLE 1-continued

Compounds of formula Ic:

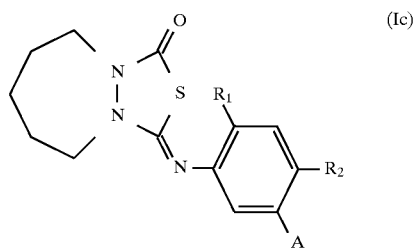

(Ic)

| Comp. No. | $R_1$ | $R_2$ | A | phys. data |
|---|---|---|---|---|
| 1.018 | F | Cl | —COOCH(CH$_3$)—CH$_2$—S—C$_2$H$_5$ | |
| 1.019 | F | Cl | —COOCH(CH$_3$)—CH$_2$—S—C$_3$H$_7$ | |
| 1.020 | F | Cl | —COOCH(CH$_3$)—CH$_2$—S—CH(CH$_3$)$_2$ | |
| 1.021 | F | Cl | —COOCH(CH$_3$)—CH$_2$—S—C$_4$H$_9$ | |
| 1.022 | F | Cl | —COOCH(CH$_3$)—CH$_2$—S—C$_5$H$_{11}$ | |
| 1.023 | F | Cl | —COOCH(CH$_3$)—CH$_2$—N(CH$_3$)$_2$ | |
| 1.024 | F | Cl | —COOCH(CH$_3$)—CH$_2$—N(C$_2$H$_5$)$_2$ | |
| 1.025 | F | Cl | —CONH$_2$ | |
| 1.026 | F | Cl | —CONH—CH$_3$ | |
| 1.027 | F | Cl | —CON(CH$_3$)$_2$ | |
| 1.028 | F | Cl | —CON(CH$_3$)(C$_4$H$_9$) | |
| 1.029 | F | Cl | —CON(CH$_2$—CH$_2$—OH)$_2$ | |
| 1.030 | F | Cl | —CONH—CH$_2$—CH=CH$_2$ | |
| 1.031 | F | Cl | —CON(CH$_2$—CH=CH$_2$)$_2$ | |
| 1.032 | F | Cl | —CON(azetidinyl) | |
| 1.033 | F | Cl | —CON(piperidinyl) | |
| 1.034 | F | Cl | —CON(morpholinyl) | |

TABLE 1-continued

Compounds of formula Ic:

(Ic)

[Structure: 7-membered ring containing N–N, fused to a 5-membered ring with C=O, S, C=N linked to a phenyl ring substituted with R₁, R₂, and A]

| Comp. No. | R₁ | R₂ | A | phys. data |
|---|---|---|---|---|
| 1.035 | F | Cl | —CON(morpholino-S) | |
| 1.036 | F | Cl | —CON(piperazino-N—CH₃) | |
| 1.037 | F | Cl | —COON=C(CH₃)(CH₃) | |
| 1.038 | F | Cl | —COOCH₂—CH₂—Cl | |
| 1.039 | F | Cl | —COOCH₂—CN | |
| 1.040 | F | Cl | —COOCH(CN)(CH₃) | |
| 1.041 | F | Cl | —COOCH₂—CH=CH₂ | |
| 1.042 | F | Cl | —COOCH₂—CH=CHCl | |
| 1.043 | F | Cl | —COOCH₂—C(Cl)=CH₂ | |
| 1.044 | F | Cl | —COOCH₂—C≡CH | |
| 1.045 | F | Cl | —COO—CH(CH₃)—C≡CH | |
| 1.046 | F | Cl | —COO-cyclopentyl | |
| 1.047 | F | Cl | —COO-cyclohexyl | |
| 1.048 | F | Cl | —COOCH₂-cyclopentyl | |
| 1.049 | F | Cl | —COOCH(CH₃)-cyclopropyl | |
| 1.050 | F | Cl | —COOCH₂-phenyl | |
| 1.051 | F | Cl | —COOCH₂-(2-chlorophenyl) | |
| 1.052 | F | Cl | —COOCH₂-(4-methylphenyl) | |
| 1.053 | F | Cl | —COSCH₃ | |
| 1.054 | F | Cl | —COSC₂H₅ | |
| 1.055 | F | Cl | —COSC₃H₇ | |
| 1.056 | F | Cl | —COS—CH₂—CH=CH₂ | |
| 1.057 | F | Cl | —COS—CH₂—COOCH₃ | |
| 1.058 | F | Cl | —COS—CH₂—COOC₂H₅ | |
| 1.059 | F | Cl | —COS—CH₂—COOC₅H₁₁ | |
| 1.060 | F | Cl | —COS—CH(CH₃)—COOCH₃ | |
| 1.061 | F | Cl | —COS—CH(CH₃)—COOC₂H₅ | |
| 1.062 | F | Cl | —COS—CH(CH₃)—COOC₃H₇ | |
| 1.063 | F | Cl | —COS—CH₂—CH₂—COOCH₃ | |
| 1.064 | F | Cl | —COS—CH₂—COOCH₂—CH₂—O—CH₃ | |
| 1.065 | F | Cl | —COOCH₂—COOCH₃ | |
| 1.066 | F | Cl | —COOCH(CH₃)—COOCH₃ | |
| 1.067 | F | Cl | —COOCH₂—COOC₅H₁₁ | |
| 1.068 | F | Cl | —COOCH₂—CH₂—Si(CH₃)₃ | |
| 1.069 | F | Cl | —COONa | |
| 1.070 | F | Cl | —COOCH₂—CH₂—O—N=C(CH₃)(CH₃) | |
| 1.071 | F | Cl | —OH | |
| 1.072 | F | Cl | —OCH₃ | |
| 1.073 | F | Cl | —OC₂H₅ | |
| 1.074 | F | Cl | —OC₃H₇ | |

TABLE 1-continued

Compounds of formula Ic:

(Ic)

| Comp. No. | $R_1$ | $R_2$ | A | phys. data |
|---|---|---|---|---|
| 1.075 | F | Cl | —OCH(CH$_3$)CH$_3$ | $n_D^{19}$ 1.5752 |
| 1.076 | F | Cl | —OC$_4$H$_9$ | |
| 1.077 | F | Cl | —OCH(CH$_3$)—C$_2$H$_5$ | |
| 1.078 | F | Cl | —O—CH$_2$—CH(CH$_3$)CH$_3$ | |
| 1.079 | F | Cl | —OCH$_2$CH═CH$_2$ | |
| 1.080 | F | Cl | —OCH$_2$—C(Cl)═CH$_2$ | |
| 1.081 | F | Cl | —OCH$_2$CH═CHCl | |
| 1.082 | F | Cl | —OCH$_2$C≡CH | |
| 1.083 | F | Cl | —OCH(CH$_3$)—C≡CH | |
| 1.084 | F | Cl | —OCH$_2$—COOCH$_3$ | |
| 1.085 | F | Cl | —O—CH$_2$—COOC$_5$H$_{11}$ | |
| 1.086 | F | Cl | —O—CH(CH$_3$)—COOCH$_3$ | |
| 1.087 | F | Cl | —O—CH$_2$—COOC$_2$H$_5$ | |
| 1.088 | F | Cl | —O—CH(CH$_3$)—COOC$_2$H$_5$ | |
| 1.089 | F | Cl | —O—CH$_2$—CH$_2$—O—CH$_3$ | |
| 1.090 | F | Cl | —O—CH(CH$_3$)—CH$_2$—S—CH$_3$ | |
| 1.091 | F | Cl | —O—CH(CH$_3$)—CH$_2$—S—C$_2$H$_5$ | |
| 1.092 | F | Cl | —O—CH(CH$_3$)—CH$_2$—S—C$_3$H$_7$ | |
| 1.093 | F | Cl | —O—CH$_2$—CH$_2$—Cl | |
| 1.094 | F | Cl | —O—CH$_2$—CN | |
| 1.095 | F | Cl | —O—CH(CH$_3$)—CN | |
| 1.096 | F | Cl | —S—CH$_3$ | |
| 1.097 | F | Cl | —S—C$_2$H$_5$ | |
| 1.098 | F | Cl | —S—C$_3$H$_7$ | |
| 1.099 | F | Cl | —S—CH(CH$_3$)CH$_3$ | |
| 1.100 | F | Cl | —S—CH$_2$—CH═CH$_2$ | |
| 1.101 | F | Cl | —S—CH$_2$—C(Cl)═CH$_2$ | |
| 1.102 | F | Cl | —S—CH$_2$—CH═CHCl | |
| 1.103 | F | Cl | —S—CH$_2$—C≡CH | |
| 1.104 | F | Cl | —S—CH(CH$_3$)—C≡CH | |
| 1.105 | F | Cl | —S—CH$_2$—COOCH$_3$ | |
| 1.106 | F | Cl | —S—CH$_2$—COOC$_2$H$_5$ | |
| 1.107 | F | Cl | —S—CH$_2$—COOC$_5$H$_{11}$ | |
| 1.108 | F | Cl | —S—CH(CH$_3$)—COOCH$_3$ | |
| 1.109 | F | Cl | —S—CH(CH$_3$)—COOC$_2$H$_5$ | |
| 1.110 | F | Cl | —S—CH$_2$—COOCH$_2$—CH$_2$—O—CH$_3$ | |
| 1.111 | F | Cl | —O—CH$_2$—C$_6$H$_5$ | |
| 1.112 | F | Cl | —S—CH$_2$—C$_6$H$_5$ | |
| 1.113 | F | Cl | —C(═N—O—CH$_3$)—CN | |
| 1.114 | F | Cl | —C(═N—O—CH$_2$—COOCH$_3$)—CN | |

TABLE 1-continued

Compounds of formula Ic:

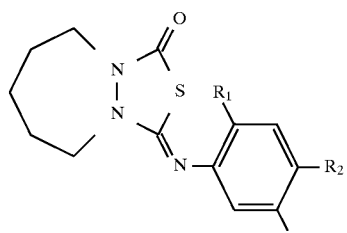

| Comp. No. | R₁ | R₂ | A | phys. data |
|---|---|---|---|---|
| 1.115 | F | Cl | —C(=N—O—CH₂—C≡CH)—CN | |
| 1.116 | F | Cl | —C(=N—O—CH₃)—CH₃ | |
| 1.117 | F | Cl | —C(=N—O—CH₂—C≡CH)—CH₃ | |
| 1.118 | F | Cl | —C(=N—O—CH₃)—CH₂—O—CH₃ | |
| 1.119 | F | Cl | —C(CH₃)(O—CH₃)(O—CH₃) | |
| 1.120 | F | Cl | —C(CH₃)(O—C₂H₅)(O—C₂H₅) | |
| 1.121 | F | Cl | —C(CH₃)(OCH₂CH₂O) (cyclic) | |
| 1.122 | F | Cl | —C(CH₃)(OCH(CH₃)CH(CH₃)O) (cyclic) | |
| 1.123 | F | Cl | —S—[cyclopropyl]—COOCH₃ | |
| 1.124 | F | Cl | —S—[cyclopropyl]—COOC₂H₅ | |
| 1.125 | F | Cl | —S—[cyclopropyl]—COOC₃H₇ | |
| 1.126 | F | Cl | —S—[cyclopropyl]—COOCH(CH₃)₂ | |
| 1.127 | F | Cl | —S—[cyclopropyl]—COO—CH₂—CH₂—Cl | |
| 1.128 | F | Cl | —S—[cyclopropyl]—COOC₅H₁₁ | |
| 1.129 | F | Cl | —S—[cyclopropyl]—COOCH₂—CH₂—O—CH₃ | |
| 1.130 | F | Cl | —S—[cyclopropyl]—COOCH(CH₃)—CH₂—S—CH₃ | |
| 1.131 | F | Cl | —S—[cyclopropyl]—COOCH(CH₃)—N(CH₃)₂ | |
| 1.132 | F | Cl | —S—[cyclopropyl]—COO-cyclopentyl | |
| 1.133 | F | Cl | —S—[cyclopropyl]—COO-cyclohexyl | |
| 1.134 | F | Cl | —S—[cyclopropyl]—COO—CH₂—CH₂—CH=CH₂ | |
| 1.135 | F | Cl | —S—[cyclopropyl]—COO—CH₂—C(Cl)=CH₂ | |
| 1.136 | F | Cl | —S—[cyclopropyl]—COO—CH₂—C≡CH | |
| 1.137 | F | Cl | —S—[cyclopropyl]—COOH | |
| 1.138 | F | Cl | —S—[cyclopropyl]—CONH₂ | |
| 1.139 | F | Cl | —S—[cyclopropyl]—CONH—CH₃ | |
| 1.140 | F | Cl | —S—[cyclopropyl]—COOC₂H₅ (with CH₃ on ring) | |

TABLE 1-continued

Compounds of formula Ic:

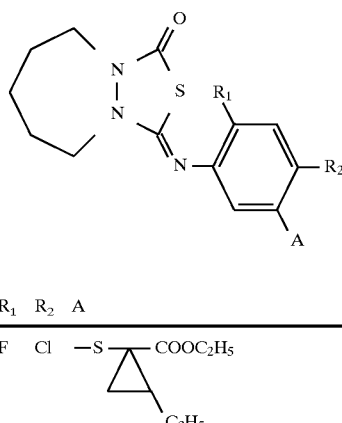

(Ic)

| Comp. No. | R₁ | R₂ | A | phys. data |
|---|---|---|---|---|
| 1.141 | F | Cl | 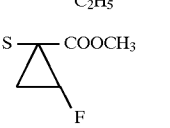 | |
| 1.142 | F | Cl | 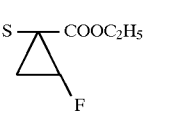 | |
| 1.143 | F | Cl | 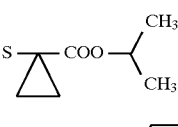 | |
| 1.144 | F | Cl | 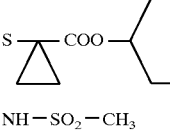 | |
| 1.145 | F | Cl | 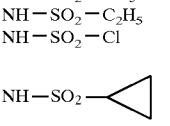 | |
| 1.146 | F | Cl | $-NH-SO_2-CH_3$ | |
| 1.147 | F | Cl | $-NH-SO_2-C_2H_5$ | |
| 1.148 | F | Cl | $-NH-SO_2-Cl$ | |
| 1.149 | F | Cl | 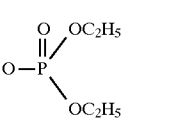 | |
| 1.150 | F | Cl | 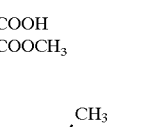 | |
| 1.151 | H | Cl | $-COOH$ | |
| 1.152 | H | Cl | $-COOCH_3$ | $n_D^{18}$ 1.6049 |
| 1.153 | H | Cl | $-COO-CH(CH_3)_2$ | |
| 1.154 | H | Cl | $-COO-C_5H_{11}$ | |
| 1.155 | H | Cl | $-COO-CH_2-CH_2-O-CH_3$ | |
| 1.156 | H | Cl | $-COOCH_2-S-CH_3$ | |
| 1.157 | H | Cl | $-COOCH(CH_3)-CH_2-S-CH_3$ | |
| 1.158 | H | Cl | $-COO-CH(CH_3)-CH_2-N(CH_3)_2$ | |
| 1.159 | H | Cl | $-CO-N(CH_3)_2$ | |
| 1.160 | H | Cl | 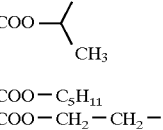 | |
| 1.161 | H | Cl | $-COON=C(CH_3)_2$ | |
| 1.162 | H | Cl | $-COOCH_2-CH_2-O-N=C(CH_3)_2$ | |
| 1.163 | H | Cl | 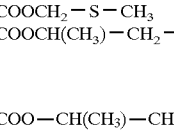 | |
| 1.164 | H | Cl |  | |
| 1.165 | H | Cl | $-S-C_3H_7$ | |
| 1.166 | H | Cl | $-COOCH_2-COOCH_3$ | |
| 1.167 | H | Cl | $-COOCH(CH_3)-COOCH_3$ | |
| 1.168 | H | Cl | $-COS-CH_2-COOCH_3$ | |
| 1.169 | H | Cl | $-COS-CH(CH_3)-COOCH_3$ | |
| 1.170 | H | Cl | $-OH$ | |
| 1.171 | H | Cl | $-OCH_3$ | |
| 1.172 | H | Cl | $-O-C_2H_5$ | |
| 1.173 | H | Cl | $-O-CH(CH_3)_2$ | |
| 1.174 | H | Cl | $-O-CH_2-C\equiv CH$ | |
| 1.175 | H | Cl | $-O-CH_2-CH=CHCl$ | |
| 1.176 | H | Cl |  | |
| 1.177 | H | Cl | $-O-CH(CH_3)-C\equiv CH$ | |
| 1.178 | H | Cl | $-O-CH_2-COOCH_3$ | |
| 1.179 | H | Cl | $-O-CH_2-COOC_2H_5$ | |

TABLE 1-continued

Compounds of formula Ic:

(Ic)

| Comp. No. | R₁ | R₂ | A | phys. data |
|---|---|---|---|---|
| 1.180 | H | Cl | —O—CH(CH₃)—COOCH₃ | |
| 1.181 | H | Cl | —SH | |
| 1.182 | H | Cl | —SCH₃ | |
| 1.183 | H | Cl | —SC₂H₅ | |
| 1.184 | H | Cl | —S—CH(CH₃)₂ | |
| 1.185 | H | Cl | —S—CH₂—COOCH₃ | |
| 1.186 | H | Cl | —S—CH(CH₃)—COOCH₃ | |
| 1.187 | H | Cl | —S—CH₂—COOC₂H₅ | |
| 1.188 | H | Cl | —C(=N—OCH₃)—CN | |
| 1.189 | H | Cl | cyclic dioxolane with CH₃ groups | |
| 1.190 | H | Cl | —S-cyclopropyl-COOC₂H₅ | |
| 1.191 | H | Cl | —S-cyclopropyl-COOH | |
| 1.192 | H | Cl | —S-cyclopropyl-COO—CH(CH₃)₂ | |
| 1.193 | H | Cl | —S-cyclopropyl(CH₃)-COOC₂H₅ | |
| 1.194 | H | Cl | —S-cyclopropyl(F)-COOC₂H₅ | |
| 1.195 | H | Cl | —S-cyclopropyl(CF₃)-COOC₂H₅ | |
| 1.196 | H | Cl | —S-cyclopropyl(CF₃)-COO—CH(CH₃)₂ | |
| 1.197 | H | Cl | —S-cyclopropyl-COOH | |
| 1.198 | H | Cl | —S-cyclopropyl(CF₃)-COOH | |
| 1.199 | H | Cl | —S-cyclopropyl(CF₃)-COOC₅H₁₁ | |
| 1.200 | H | Cl | —S-cyclopropyl(C₂H₅)-COOC₂H₅ | |
| 1.201 | H | Cl | —S-cyclopropyl(CH(CH₃)₂)-COOC₂H₅ | |
| 1.202 | H | Cl | —NH—SO₂—C₂H₅ | |
| 1.203 | H | Cl | —NH—SO₂—CH₂—Cl | |
| 1.204 | F | CN | —COOH | |
| 1.205 | F | CN | —COO—CH(CH₃)₂ | |
| 1.206 | F | CN | —O—CH(CH₃)₂ | |
| 1.207 | F | CN | —O—CH₂—C≡CH | |
| 1.208 | F | CN | —O—CH(CH₃)—C≡CH | |
| 1.209 | F | CN | —S—CH₂—COOCH₃ | |
| 1.210 | F | CN | —S—CH(CH₃)—COOCH₃ | |
| 1.211 | F | CN | —O—CH₂—COOCH₃ | |
| 1.212 | F | CN | —O—CH₂—COOC₅H₁₁ | |
| 1.213 | F | CN | —O—CH(CH₃)—COOC₂H₅ | |

TABLE 1-continued

Compounds of formula Ic:

(Ic)

| Comp. No. | R₁ | R₂ | A | phys. data |
|---|---|---|---|---|
| 1.214 | F | CN | —S—△—COOCH₃ | |
| 1.215 | F | CN | —S—△—COOC₂H₅ | |
| 1.216 | F | CN | —S—△(F)—COOC₂H₅ | |
| 1.217 | F | CN | —S—△—COOH | |
| 1.218 | F | CN | —S—△(F)—COOH | |
| 1.219 | F | CN | —S—△(CF₃)—COOH | |
| 1.220 | F | CN | —S—△—COOC₂H₅ | |
| 1.221 | F | Br | —COOH | |
| 1.222 | F | Br | —COO—CH(CH₃)₂ | |
| 1.223 | F | Br | —OH | |
| 1.224 | F | Br | —O—CH(CH₃)₂ | |
| 1.225 | F | Br | —O—CH₂—C≡CH | |
| 1.226 | F | Br | —O—CH(CH₃)—C≡CH | |
| 1.227 | F | Br | —O—CH₂COOCH₃ | |
| 1.228 | F | Br | —O—CH₂—COOC₅H₁₁ | |
| 1.229 | F | Br | —S—CH₂—COOCH₃ | |

TABLE 1-continued

Compounds of formula Ic:

(Ic)

| Comp. No. | R₁ | R₂ | A | phys. data |
|---|---|---|---|---|
| 1.230 | F | Br | —S—△—COOC₂H₅ | |
| 1.231 | F | Br | —S—△(F)—COOH | |
| 1.232 | F | Br | —S—△(F)—COOC₂H₅ | |
| 1.233 | F | Cl | —O—(oxetanyl) | |
| 1.234 | H | Cl | —O—(oxetanyl) | |
| 1.235 | F | Cl | —C(O)—O—(oxetanyl) | |
| 1.236 | H | Cl | —C(O)—O—(oxetanyl) | |
| 1.237 | H | Cl | H | resin |

TABLE 2

Compounds of formula Id:

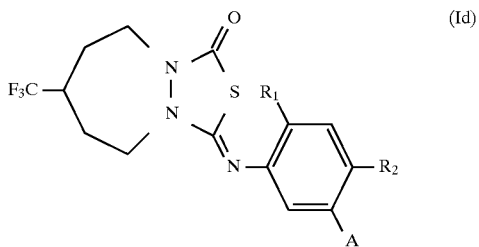

| Comp. No. | R₁ | R₂ | A | phys. data |
|---|---|---|---|---|
| 2.001 | F | Cl | —H | |
| 2.002 | F | Cl | —CN | |
| 2.003 | F | Cl | —NO₂ | |
| 2.004 | F | Cl | —COOH | |
| 2.005 | F | Cl | —COOCH₃ | m.p. 75° C. |
| 2.006 | F | Cl | —COOC₂H₅ | |
| 2.007 | F | Cl | —COOC₃H₇ | |
| 2.008 | F | Cl | —COOCH(CH₃)₂ | $n_D^{18}$ 1.5572 |
| 2.009 | F | Cl | —COOC₄H₉ | |
| 2.010 | F | Cl | —COOCH(CH₃)—CH₂—CH₃ | |
| 2.011 | F | Cl | —COOCH₂—CH₂—CH(CH₃)₂ | |
| 2.012 | F | Cl | —COOC₅H₁₁ | |
| 2.013 | F | Cl | —COOCH₂—CH₂—O—CH₃ | |
| 2.014 | F | Cl | —COOCH₂—CH₂—O—C₂H₅ | |
| 2.015 | F | Cl | —COOCH(CH₃)—CH₂—OCH₃ | |
| 2.016 | F | Cl | —COOCH₂—CH₂—S—CH₃ | |
| 2.017 | F | Cl | —COOCH(CH₃)—CH₂—S—CH₃ | |
| 2.018 | F | Cl | —COOCH(CH₃)—CH₂—S—C₂H₅ | |
| 2.019 | F | Cl | —COOCH(CH₃)—CH₂—S—C₃H₇ | |
| 2.020 | F | Cl | —COOCH(CH₃)—CH₂—S—CH(CH₃)₂ | |
| 2.021 | F | Cl | —COOCH(CH₃)—CH₂—S—C₄H₉ | |
| 2.022 | F | Cl | —COOCH(CH₃)—CH₂—S—C₅H₁₁ | |
| 2.023 | F | Cl | —COOCH(CH₃)—CH₂—N(CH₃)₂ | |
| 2.024 | F | Cl | —COOCH(CH₃)—CH₂—N(C₂H₅)₂ | |
| 2.025 | F | Cl | —CONH₂ | |
| 2.026 | F | Cl | —CONH—CH₃ | |
| 2.027 | F | Cl | —CON(CH₃)₂ | |
| 2.028 | F | Cl | —CON(CH₃)(C₄H₉) | |

TABLE 2-continued

Compounds of formula Id:

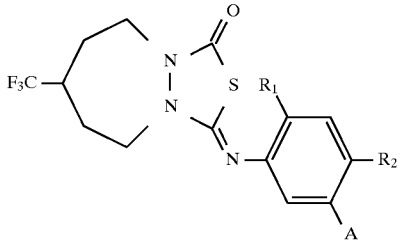

| Comp. No. | R₁ | R₂ | A | phys. data |
|---|---|---|---|---|
| 2.029 | F | Cl | —CON(CH₂—CH₂—OH)₂ | |
| 2.030 | F | Cl | —CONH—CH₂—CH=CH₂ | |
| 2.031 | F | Cl | —CON(CH₂—CH=CH₂)₂ | |
| 2.032 | F | Cl | —CON(pyrrolidine) | |
| 2.033 | F | Cl | —CON(piperidine) | |
| 2.034 | F | Cl | —CON(morpholine) | |
| 2.035 | F | Cl | —CON(thiomorpholine) | |
| 2.036 | F | Cl | —CON(N-methylpiperazine) | |
| 2.037 | F | Cl | —COON=C(CH₃)₂ | |
| 2.038 | F | Cl | —COOCH₂CH₂—Cl | |
| 2.039 | F | Cl | —COOCH₂—CN | |
| 2.040 | F | Cl | —COOCH(CN)(CH₃) | |
| 2.041 | F | Cl | —COOCH₂—CH=CH₂ | |
| 2.042 | F | Cl | —COOCH₂—CH=CHCl | |
| 2.043 | F | Cl | —COOCH₂—C(Cl)=CH₂ | |
| 2.044 | F | Cl | —COOCH₂—C≡CH | |

TABLE 2-continued

Compounds of formula Id:

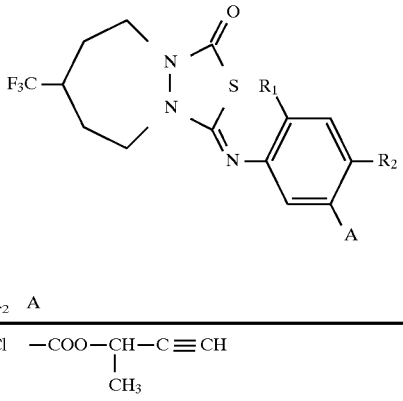

(Id)

| Comp. No. | R₁ | R₂ | A | phys. data |
|---|---|---|---|---|
| 2.045 | F | Cl | —COO—CH(CH₃)—C≡CH | |
| 2.046 | F | Cl | —COO-cyclopentyl | |
| 2.047 | F | Cl | —COO-cyclohexyl | |
| 2.048 | F | Cl | —COOCH₂-cyclopentyl | |
| 2.049 | F | Cl | —COOCH(CH₃)-cyclopropyl | |
| 2.050 | F | Cl | —COOCH₂-phenyl | |
| 2.051 | F | Cl | —COOCH₂-(2-chlorophenyl) | |
| 2.052 | F | Cl | —COOCH₂-(4-methylphenyl) | |
| 2.053 | F | Cl | —COSCH₃ | |
| 2.054 | F | Cl | —COSC₂H₅ | |
| 2.055 | F | Cl | —COSC₃H₇ | |
| 2.056 | F | Cl | —COS—CH₂—CH═CH₂ | |
| 2.057 | F | Cl | —COS—CH₂—COOCH₃ | |
| 2.058 | F | Cl | —COS—CH₂—COOC₂H₅ | |
| 2.059 | F | Cl | —COS—CH₂—COOC₅H₁₁ | |
| 2.060 | F | Cl | —COS—CH(CH₃)—COOCH₃ | |
| 2.061 | F | Cl | —COS—CH(CH₃)—COOC₂H₅ | |

TABLE 2-continued

Compounds of formula Id:

$$\text{(Id)}$$

| Comp. No. | R₁ | R₂ | A | phys. data |
|---|---|---|---|---|
| 2.062 | F | Cl | —COS—CH(CH₃)—COOC₃H₇ | |
| 2.063 | F | Cl | —COS—CH₂—CH₂—COOCH₃ | |
| 2.064 | F | Cl | —COS—CH₂—COOCH₂—CH₂—O—CH₃ | |
| 2.065 | F | Cl | —COOCH₂—COOCH₃ | |
| 2.066 | F | Cl | —COOCH(CH₃)—COOCH₃ | |
| 2.067 | F | Cl | —COOCH₂—COOC₅H₁₁ | |
| 2.068 | F | Cl | —COOCH₂—CH₂—Si(CH₃)₃ | |
| 2.069 | F | Cl | —COONa | |
| 2.070 | F | Cl | —COOCH₂—CH₂—O—N=C(CH₃)₂ | |
| 2.071 | F | Cl | —OH | |
| 2.072 | F | Cl | —OCH₃ | |
| 2.073 | F | Cl | —OC₂H₅ | |
| 2.074 | F | Cl | —OC₃H₇ | |
| 2.075 | F | Cl | —OCH(CH₃)₂ | |
| 2.076 | F | Cl | —OC₄H₉ | |
| 2.077 | F | Cl | —OCH(CH₃)—C₂H₅ | |
| 2.078 | F | Cl | —O—CH₂—CH(CH₃)₂ | |
| 2.079 | F | Cl | —OCH₂CH=CH₂ | |
| 2.080 | F | Cl | —OCH₂—C(Cl)=CH₂ | |
| 2.081 | F | Cl | —OCH₂CH=CHCl | |
| 2.082 | F | Cl | —OCH₂C≡CH | resin |
| 2.083 | F | Cl | —OCH(CH₃)—C≡CH | |
| 2.084 | F | Cl | —OCH₂—COOCH₃ | |
| 2.085 | F | Cl | —O—CH₂—COOC₅H₁₁ | |

TABLE 2-continued

Compounds of formula Id:

$$\text{(Id)}$$

(structure: a seven-membered ring containing N–N with F$_3$C substituent; N attached to C(=O)–; ring N connected via C(=N–Ar)–S–R$_1$, where Ar is a phenyl bearing R$_2$ and A)

| Comp. No. | R$_1$ | R$_2$ | A | phys. data |
|---|---|---|---|---|
| 2.086 | F | Cl | —O—CH(CH$_3$)—COOCH$_3$ | |
| 2.087 | F | Cl | —O—CH$_2$—COOC$_2$H$_5$ | |
| 2.088 | F | Cl | —O—CH(CH$_3$)—COOC$_2$H$_5$ | |
| 2.089 | F | Cl | O—CH$_2$—CH$_2$—O—CH$_3$ | |
| 2.090 | F | Cl | —O—CH(CH$_3$)—CH$_2$—S—CH$_3$ | |
| 2.091 | F | Cl | —O—CH(CH$_3$)—CH$_2$—S—C$_2$H$_5$ | |
| 2.092 | F | Cl | —O—CH(CH$_3$)—CH$_2$—S—C$_3$H$_7$ | |
| 2.093 | F | Cl | —O—CH$_2$—CH$_2$—Cl | |
| 2.094 | F | Cl | —O—CH$_2$CN | |
| 2.095 | F | Cl | —O—CH(CH$_3$)—CN | |
| 2.096 | F | Cl | —S—CH$_3$ | |
| 2.097 | F | Cl | —S—C$_2$H$_5$ | |
| 2.098 | F | Cl | —S—C$_3$H$_7$ | |
| 2.099 | F | Cl | —S—CH(CH$_3$)$_2$ | |
| 2.100 | F | Cl | —S—CH$_2$—CH=CH$_2$ | |
| 2.101 | F | Cl | —S—CH$_2$—C(Cl)=CH$_2$ | |
| 2.102 | F | Cl | —S—CH$_2$—CH=CHCl | |
| 2.103 | F | Cl | —S—CH$_2$—C≡CH | |
| 2.104 | F | Cl | —S—CH(CH$_3$)—C≡CH | |
| 2.105 | F | Cl | —S—CH$_2$—COOCH$_3$ | $n_D^{18}$ 1.5719 |
| 2.106 | F | Cl | —S—CH$_2$—COOC$_2$H$_5$ | |
| 2.107 | F | Cl | —S—CH$_2$—COOC$_5$H$_{11}$ | |
| 2.108 | F | Cl | —S—CH(CH$_3$)—COOCH$_3$ | |

TABLE 2-continued

Compounds of formula Id:

$$\text{(Id)}$$

(Structure: F$_3$C-substituted 7-membered ring with two N atoms, N-C(=O) group, and C=N connected to phenyl ring bearing R$_1$, R$_2$, and A substituents; S-R$_1$ on the central C)

| Comp. No. | R$_1$ | R$_2$ | A | phys. data |
|---|---|---|---|---|
| 2.109 | F | Cl | —S—CH(CH$_3$)—COOC$_2$H$_5$ | |
| 2.110 | F | Cl | —S—CH$_2$—COOCH$_2$—CH$_2$—O—CH$_3$ | |
| 2.111 | F | Cl | —O—CH$_2$—C$_6$H$_5$ | |
| 2.112 | F | Cl | —S—CH$_2$—C$_6$H$_5$ | |
| 2.113 | F | Cl | —C(=N—O—CH$_3$)—CN | |
| 2.114 | F | Cl | —C(=N—O—CH$_2$—COOCH$_3$)—CN | |
| 2.115 | F | Cl | —C(=N—O—CH$_2$—C≡CH)—CN | |
| 2.116 | F | Cl | —C(=N—O—CH$_3$)—CH$_3$ | |
| 2.117 | F | Cl | —C(=N—O—CH$_2$—C≡CH)—CH$_3$ | |
| 2.118 | F | Cl | —C(=N—O—CH$_3$)—CH$_2$—O—CH$_3$ | |
| 2.119 | F | Cl | —C(CH$_3$)(O—CH$_3$)(O—CH$_3$) | |
| 2.120 | F | Cl | —C(CH$_3$)(O—C$_2$H$_5$)(O—C$_2$H$_5$) | |
| 2.121 | F | Cl | —C(CH$_3$)(O—CH$_2$—O) (cyclic) | |

TABLE 2-continued

Compounds of formula Id:

$$\text{(Id)}$$

| Comp. No. | $R_1$ | $R_2$ | A | phys. data |
|---|---|---|---|---|
| 2.122 | F | Cl | (dimethyl dioxolane with CH₃ groups) | |
| 2.123 | F | Cl | —S—(cyclopropyl)—COOCH₃ | |
| 2.124 | F | Cl | —S—(cyclopropyl)—COOC₂H₅ | |
| 2.125 | F | Cl | —S—(cyclopropyl)—COOC₃H₇ | |
| 2.126 | F | Cl | —S—(cyclopropyl)—COOCH(CH₃)₂ | |
| 2.127 | F | Cl | —S—(cyclopropyl)—COO—CH₂—CH₂—Cl | |
| 2.128 | F | Cl | —S—(cyclopropyl)—COOC₅H₁₁ | |
| 2.129 | F | Cl | —S—(cyclopropyl)—COOCH₂—CH₂—O—CH₃ | |
| 2.130 | F | Cl | —S—(cyclopropyl)—COOCH(CH₃)—CH₂—S—CH₃ | |
| 2.131 | F | Cl | —S—(cyclopropyl)—COOCH(CH₃)—N(CH₃)₂ | |
| 2.132 | F | Cl | —S—(cyclopropyl)—COO—(cyclopentyl) | |
| 2.133 | F | Cl | —S—(cyclopropyl)—COO—(cyclohexyl) | |
| 2.134 | F | Cl | —S—(cyclopropyl)—COO—CH₂—CH₂—CH=CH₂ | |

TABLE 2-continued

Compounds of formula Id:

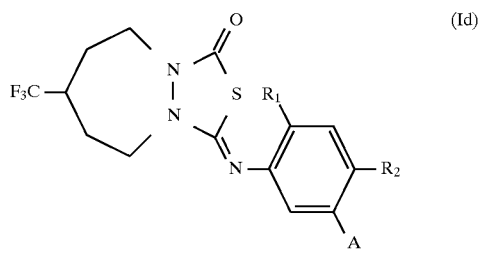

| Comp. No. | R₁ | R₂ | A | phys. data |
|---|---|---|---|---|
| 2.135 | F | Cl | −S−△−COO−CH₂−C(Cl)=CH₂ | |
| 2.136 | F | Cl | −S−△−COO−CH₂−C≡CH | |
| 2.137 | F | Cl | −S−△−COOH | m.p. 95° C.(decomp.) |
| 2.138 | F | Cl | −S−△−CONH₂ | |
| 2.139 | F | Cl | −S−△−COONH−CH₃ | |
| 2.140 | F | Cl | −S−△(CH₃)−COOC₂H₅ | |
| 2.141 | F | Cl | −S−△(C₂H₅)−COOC₂H₅ | |
| 2.142 | F | Cl | −S−△(F)−COOCH₃ | |
| 2.143 | F | Cl | −S−△(F)−COOC₂H₅ | |
| 2.144 | F | Cl | −S−△−COO−CH(CH₃)₂ | |
| 2.145 | F | Cl | −S−△−COO−cyclopentyl | |
| 2.146 | F | Cl | −NH−SO₂−CH₃ | |
| 2.147 | F | Cl | −NH−SO₂−C₂H₅ | |
| 2.148 | F | Cl | −NH−SO₂−Cl | |
| 2.149 | F | Cl | −NH−SO₂−△ | |
| 2.150 | F | Cl | −O−P(=O)(OC₂H₅)(OC₂H₅) | |

TABLE 2-continued

Compounds of formula Id:

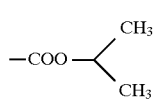

| Comp. No. | R₁ | R₂ | A | phys. data |
|---|---|---|---|---|
| 2.151 | H | Cl | —COOH | m.p. 190° C. |
| 2.152 | H | Cl | —COOCH₃ | resin |
| 2.153 | H | Cl | —COO—CH(CH₃)₂ | |
| 2.154 | H | Cl | —COO—C₅H₁₁ | |
| 2.155 | H | Cl | —COO—CH₂—CH₂—O—CH₃ | |
| 2.156 | H | Cl | —COOCH₂—S—CH₃ | |
| 2.157 | H | Cl | —COOCH(CH₃)—CH₂—S—CH₃ | |
| 2.158 | H | Cl | —COO—CH(CH₃)—CH₂—N(CH₃)₂ | |
| 2.159 | H | Cl | —CO—N(CH₃)₂ | |
| 2.160 | H | Cl | —CO—N(morpholino) | |
| 2.161 | H | Cl | —COON=C(CH₃)₂ | |
| 2.162 | H | Cl | —COOCH₂—CH₂—O—N=C(CH₃)₂ | |
| 2.163 | H | Cl | —COO—cyclohexyl | |
| 2.164 | H | Cl | —CH(CH₃)—cyclopropyl | |
| 2.165 | H | Cl | —S—C₃H₇ | |
| 2.166 | H | Cl | —COOCH₂—COOCH₃ | |
| 2.167 | H | Cl | —COOCH(CH₃)—COOCH₃ | |
| 2.168 | H | Cl | —COS—CH₂—COOCH₃ | |
| 2.169 | H | Cl | —COS—CH(CH₃)—COOCH₃ | |
| 2.170 | H | Cl | —OH | |
| 2.171 | H | Cl | —OCH₃ | |
| 2.172 | H | Cl | —O—C₂H₅ | |

TABLE 2-continued

Compounds of formula Id:

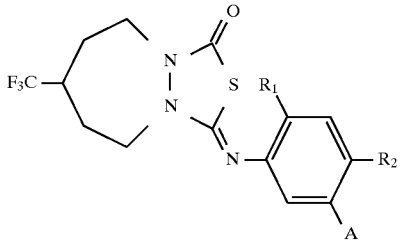

(Id)

| Comp. No. | R₁ | R₂ | A | phys. data |
|---|---|---|---|---|
| 2.173 | H | Cl | —O—CH(CH₃)₂ | |
| 2.174 | H | Cl | —O—CH₂—C≡CH | |
| 2.175 | H | Cl | —O—CH₂—CH=CHCl | |
| 2.176 | H | Cl | —O—CH₂—C(Cl)=CH₂ | |
| 2.177 | H | Cl | —O—CH(CH₃)—C≡CH | |
| 2.178 | H | Cl | —O—CH₂—COOCH₃ | |
| 2.179 | H | Cl | —O—CH₂—COOC₂H₅ | |
| 2.180 | H | Cl | —O—CH(CH₃)—COOCH₃ | |
| 2.181 | H | Cl | —SH | |
| 2.182 | H | Cl | —SCH₃ | |
| 2.183 | H | Cl | —SC₂H₅ | |
| 2.184 | H | Cl | —S—CH(CH₃)₂ | |
| 2.185 | H | Cl | —S—CH₂—COOCH₃ | |
| 2.186 | H | Cl | —S—CH(CH₃)—COOCH₃ | |
| 2.187 | H | Cl | —S—CH₂—COOC₂H₅ | |
| 2.188 | H | Cl | —C(=N—OCH₃)—CN | |
| 2.189 | H | Cl | 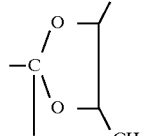 | |
| 2.190 | H | Cl | —S—(cyclopropyl)—COOC₂H₅ | |
| 2.191 | H | Cl | —S—(cyclopropyl)—COOH | |
| 2.192 | H | Cl | —S—(cyclopropyl)—COO—CH(CH₃)₂ | |

TABLE 2-continued

Compounds of formula Id:

$$\text{(Id)}$$

(structure: F$_3$C-substituted 7-membered ring with N–N, C(=O), S, C=N, attached to phenyl bearing R$_1$, R$_2$, A substituents)

| Comp. No. | R$_1$ | R$_2$ | A | phys. data |
|---|---|---|---|---|
| 2.193 | H | Cl | –S–(cyclopropyl with COOC$_2$H$_5$ and CH$_3$) | |
| 2.194 | H | Cl | –S–(cyclopropyl with COOC$_2$H$_5$ and F) | |
| 2.195 | H | Cl | –S–(cyclopropyl with COOC$_2$H$_5$ and CF$_3$) | |
| 2.196 | H | Cl | –S–(cyclopropyl with COO–CH(CH$_3$)$_2$ and CF$_3$) | |
| 2.197 | H | Cl | –S–(cyclopropyl with COOH) | |
| 2.198 | H | Cl | –S–(cyclopropyl with COOH and CF$_3$) | |
| 2.199 | H | Cl | –S–(cyclopropyl with COOC$_5$H$_{11}$ and CF$_3$) | |
| 2.200 | H | Cl | –S–(cyclopropyl with COOC$_2$H$_5$ and C$_2$H$_5$) | |
| 2.201 | H | Cl | –S–(cyclopropyl with COOC$_2$H$_5$ and CH(CH$_3$)$_2$) | |
| 2.202 | H | Cl | –NH–SO$_2$–C$_2$H$_5$ | |
| 2.203 | H | Cl | –NH–SO$_2$–CH$_2$–Cl | |
| 2.204 | F | CN | –COOH | |
| 2.205 | F | CN | –COO–CH(CH$_3$)$_2$ | |

TABLE 2-continued

Compounds of formula Id:

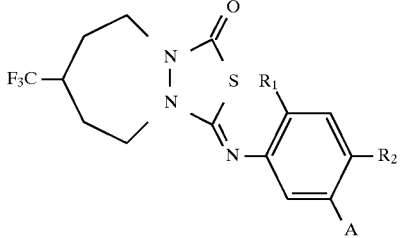

| Comp. No. | $R_1$ | $R_2$ | A | phys. data |
|---|---|---|---|---|
| 2.206 | F | CN | —O—CH(CH$_3$)$_2$ | |
| 2.207 | F | CN | —O—CH$_2$—C≡CH | |
| 2.208 | F | CN | —O—CH(CH$_3$)—C≡CH | |
| 2.209 | F | CN | —S—CH$_2$—COOCH$_3$ | |
| 2.210 | F | CN | —S—CH(CH$_3$)—COOCH$_3$ | |
| 2.211 | F | CN | —O—CH$_2$—COOCH$_3$ | |
| 2.212 | F | CN | —O—CH$_2$—COOC$_5$H$_{11}$ | |
| 2.213 | F | CN | —O—CH(CH$_3$)—COOC$_2$H$_5$ | |
| 2.214 | F | CN | —S—(cyclopropyl)—COOCH$_3$ | |
| 2.215 | F | CN | —S—(cyclopropyl)—COOC$_2$H$_5$ | |
| 2.216 | F | CN | —S—(cyclopropyl-F)—COOC$_2$H$_5$ | |
| 2.217 | F | CN | —S—(cyclopropyl)—COOH | |
| 2.218 | F | CN | —S—(cyclopropyl-F)—COOH | |
| 2.219 | F | CN | —S—(cyclopropyl-CF$_3$)—COOH | |
| 2.220 | F | CN | —S—(cyclopropyl)—COOC$_2$H$_5$ | |
| 2.221 | F | Br | —COOH | |
| 2.222 | F | Br | —COO—CH(CH$_3$)$_2$ | |
| 2.223 | F | Br | —OH | |
| 2.224 | F | Br | —O—CH(CH$_3$)$_2$ | |

TABLE 2-continued
Compounds of formula Id:
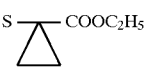
(Id)
| Comp. No. | R₁ | R₂ | A | phys. data |
|---|---|---|---|---|
| 2.225 | F | Br | —O—CH₂—C≡CH | |
| 2.226 | F | Br | —O—CH(CH₃)—C≡CH | |
| 2.227 | F | Br | —O—CH₂COOCH₃ | |
| 2.228 | F | Br | —O—CH₂—COOC₅H₁₁ | |
| 2.229 | F | Br | —S—CH₂—COOCH₃ | |
| 2.230 | F | Br | 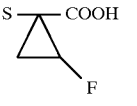 | |
| 2.231 | F | Br | 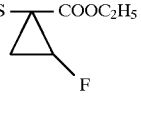 | |
| 2.232 | F | Br | 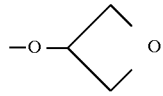 | |
| 2.233 | F | Cl | 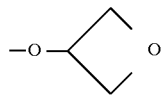 | |
| 2.234 | H | Cl | 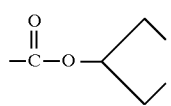 | |
| 2.235 | F | Cl | 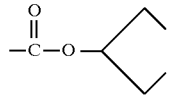 | |
| 2.236 | H | Cl |  | |
| 2.237 | H | Cl | H | $n_D^{18}$ 1.5826 |

TABLE 3

Compounds of formula Ie:

(Ie)

[Structure: 1,2-diazepane with isopropyl-CH substituent, N-C(=O), N=C-S-aryl group where aryl has R1, R2, A substituents]

| Comp. No. | R₁ | R₂ | A | phys. data |
|---|---|---|---|---|
| 3.001 | F | Cl | —H | |
| 3.002 | F | Cl | —CN | |
| 3.003 | F | Cl | —NO₂ | |
| 3.004 | F | Cl | —COOH | |
| 3.005 | F | Cl | —COOCH₃ | |
| 3.006 | F | Cl | —COOC₂H₅ | |
| 3.007 | F | Cl | —COOC₃H₇ | |
| 3.008 | F | Cl | —COOCH(CH₃)₂ | |
| 3.009 | F | Cl | —COOC₄H₉ | |
| 3.010 | F | Cl | —COOCH(CH₃)—CH₂—CH₃ | |
| 3.011 | F | Cl | —COOCH₂—CH₂—CH(CH₃)₂ | |
| 3.012 | F | Cl | —COOC₅H₁₁ | |
| 3.013 | F | Cl | —COOCH₂—CH₂—O—CH₃ | |
| 3.014 | F | Cl | —COOCH₂—CH₂—O—C₂H₅ | |
| 3.015 | F | Cl | —COOCH(CH₃)—CH₂—OCH₃ | |
| 3.016 | F | Cl | —COOCH₂—CH₂—S—CH₃ | |
| 3.017 | F | Cl | —COOCH(CH₃)—CH₂—S—CH₃ | |
| 3.018 | F | Cl | —COOCH(CH₃)—CH₂—S—C₂H₅ | |
| 3.019 | F | Cl | —COOCH(CH₃)—CH₂—S—C₃H₇ | |
| 3.020 | F | Cl | —COOCH(CH₃)—CH₂—S—CH(CH₃)₂ | |
| 3.021 | F | Cl | —COOCH(CH₃)—CH₂—S—C₄H₉ | |
| 3.022 | F | Cl | —COOCH(CH₃)—CH₂—S—C₅H₁₁ | |
| 3.023 | F | Cl | —COOCH(CH₃)—CH₂—N(CH₃)₂ | |
| 3.024 | F | Cl | —COOCH(CH₃)—CH₂—N(C₂H₅)₂ | |
| 3.025 | F | Cl | —CONH₂ | |
| 3.026 | F | Cl | —CONH—CH₃ | |
| 3.027 | F | Cl | —CON(CH₃)₂ | |
| 3.028 | F | Cl | —CON(CH₃)(C₄H₉) | |
| 3.029 | F | Cl | —CON(CH₂—CH₂—OH)₂ | |
| 3.030 | F | Cl | —CONH—CH₂—CH=CH₂ | |
| 3.031 | F | Cl | —CON(CH₂—CH=CH₂)₂ | |
| 3.032 | F | Cl | —CON(pyrrolidinyl) | |
| 3.033 | F | Cl | —CON(piperidinyl) | |
| 3.034 | F | Cl | —CON(morpholinyl) | |
| 3.035 | F | Cl | —CON(thiomorpholinyl) | |
| 3.036 | F | Cl | —CON(4-methylpiperazinyl) | |
| 3.037 | F | Cl | —COON=C(CH₃)₂ | |
| 3.038 | F | Cl | —COOCH₂—CH₂—Cl | |
| 3.039 | F | Cl | —COOCH₂—CN | |
| 3.040 | F | Cl | —COOCH(CN)(CH₃) | |
| 3.041 | F | Cl | —COOCH₂—CH=CH₂ | |
| 3.042 | F | Cl | —COOCH₂—CH=CHCl | |
| 3.043 | F | Cl | —COOCH₂—C(Cl)=CH₂ | |

TABLE 3-continued

Compounds of formula Ie:

(Ie)

| Comp. No. | R₁ | R₂ | A | phys. data |
|---|---|---|---|---|
| 3.044 | F | Cl | —COOCH₂—C≡CH | |
| 3.045 | F | Cl | —COO—CH(CH₃)—C≡CH | |
| 3.046 | F | Cl | —COO-cyclopentyl | |
| 3.047 | F | Cl | —COO-cyclohexyl | |
| 3.048 | F | Cl | —COOCH₂-cyclopentyl | |
| 3.049 | F | Cl | —COOCH(CH₃)-cyclopropyl | |
| 3.050 | F | Cl | —COOCH₂-phenyl | |
| 3.051 | F | Cl | —COOCH₂-(2-Cl-phenyl) | |
| 3.052 | F | Cl | —COOCH₂-(4-CH₃-phenyl) | |
| 3.053 | F | Cl | —COSCH₃ | |
| 3.054 | F | Cl | —COSC₂H₅ | |
| 3.055 | F | Cl | —COSC₃H₇ | |
| 3.056 | F | Cl | —COS—CH₂—CH=CH₂ | |
| 3.057 | F | Cl | —COS—CH₂—COOCH₃ | |
| 3.058 | F | Cl | —COS—CH₂—COOC₂H₅ | |
| 3.059 | F | Cl | —COS—CH₂—COOC₅H₁₁ | |
| 3.060 | F | Cl | —COS—CH(CH₃)—COOCH₃ | |
| 3.061 | F | Cl | —COS—CH(CH₃)—COOC₂H₅ | |
| 3.062 | F | Cl | —COS—CH(CH₃)—COOC₃H₇ | |
| 3.063 | F | Cl | —COS—CH₂—CH₂—COOCH₃ | |
| 3.064 | F | Cl | —COS—CH₂—COOCH₂—CH₂—O—CH₃ | |
| 3.065 | F | Cl | —COOCH₂—COOCH₃ | |
| 3.066 | F | Cl | —COOCH(CH₃)—COOCH₃ | |
| 3.067 | F | Cl | —COOCH₂—COOC₅H₁₁ | |
| 3.068 | F | Cl | —COOCH₂—CH₂—Si(CH₃)₃ | |
| 3.069 | F | Cl | —COONa | |
| 3.070 | F | Cl | —COOCH₂—CH₂—O—N=C(CH₃)₂ | |
| 3.071 | F | Cl | —OH | |
| 3.072 | F | Cl | —OCH₃ | |
| 3.073 | F | Cl | —OC₂H₅ | |
| 3.074 | F | Cl | —OC₃H₇ | |
| 3.075 | F | Cl | —OCH(CH₃)₂ | |
| 3.076 | F | Cl | —OC₄H₉ | |
| 3.077 | F | Cl | —OCH(CH₃)—C₂H₅ | |
| 3.078 | F | Cl | —O—CH₂—CH(CH₃)₂ | |
| 3.079 | F | Cl | —OCH₂CH=CH₂ | |
| 3.080 | F | Cl | —OCH₂—C(Cl)=CH₂ | |
| 3.081 | F | Cl | —OCH₂CH=CHCl | |
| 3.082 | F | Cl | —OCH₂C≡CH | |
| 3.083 | F | Cl | —OCH(CH₃)—C≡CH | |

TABLE 3-continued

Compounds of formula Ie:

(Ie)

| Comp. No. | R₁ | R₂ | A | phys. data |
|---|---|---|---|---|
| 3.084 | F | Cl | —OCH₂—COOCH₃ | |
| 3.085 | F | Cl | —O—CH₂—COOC₅H₁₁ | |
| 3.086 | F | Cl | —O—CH(CH₃)—COOCH₃ | |
| 3.087 | F | Cl | —O—CH₂—COOC₂H₅ | |
| 3.088 | F | Cl | —O—CH(CH₃)—COOC₂H₅ | |
| 3.089 | F | Cl | —O—CH₂—CH₂—O—CH₃ | |
| 3.090 | F | Cl | —O—CH(CH₃)—CH₂—S—CH₃ | |
| 3.091 | F | Cl | —O—CH(CH₃)—CH₂—S—C₂H₅ | |
| 3.092 | F | Cl | —O—CH(CH₃)—CH₂—S—C₃H₇ | |
| 3.093 | F | Cl | —O—CH₂—CH₂—Cl | |
| 3.094 | F | Cl | —O—CH₂—CN | |
| 3.095 | F | Cl | —O—CH(CH₃)—CN | |
| 3.096 | F | Cl | —S—CH₃ | |
| 3.097 | F | Cl | —S—C₂H₅ | |
| 3.098 | F | Cl | —S—C₃H₇ | |
| 3.099 | F | Cl | —S—CH(CH₃)₂ | |
| 3.100 | F | Cl | —S—CH₂—CH=CH₂ | |
| 3.101 | F | Cl | —S—CH₂—C(Cl)=CH₂ | |
| 3.102 | F | Cl | —S—CH₂—CH=CHCl | |
| 3.103 | F | Cl | —S—CH₂—C≡CH | |
| 3.104 | F | Cl | —S—CH(CH₃)—C≡CH | |
| 3.105 | F | Cl | —S—CH₂—COOCH₃ | |
| 3.106 | F | Cl | —S—CH₂—COOC₂H₅ | |
| 3.107 | F | Cl | —S—CH₂—COOC₅H₁₁ | |
| 3.108 | F | Cl | —S—CH(CH₃)—COOCH₃ | |
| 3.109 | F | Cl | —S—CH(CH₃)—COOC₂H₅ | |
| 3.110 | F | Cl | —S—CH₂—COOCH₂—CH₂—O—CH₃ | |
| 3.111 | F | Cl | —O—CH₂—C₆H₅ | |
| 3.112 | F | Cl | —S—CH₂—C₆H₅ | |
| 3.113 | F | Cl | —C(=N—O—CH₃)—CN | |
| 3.114 | F | Cl | —C(=N—O—CH₂—COOCH₃)—CN | |
| 3.115 | F | Cl | —C(=N—O—CH₂—C≡CH)—CN | |
| 3.116 | F | Cl | —C(=N—O—CH₃)—CH₂ | |
| 3.117 | F | Cl | —C(=N—O—CH₂—C≡CH)—CH₃ | |
| 3.118 | F | Cl | —C(=N—O—CH₃)—CH₂—O—CH₃ | |
| 3.119 | F | Cl | —C(CH₃)(O—CH₃)(O—CH₃) | |
| 3.120 | F | Cl | —C(CH₃)(O—C₂H₅)(O—C₂H₅) | |

TABLE 3-continued

Compounds of formula Ie:

(Ie) — structure with isopropyl-substituted 7-membered ring containing N-N, C=O, and C=N linked to phenyl bearing R₁, R₂, A substituents.

| Comp. No. | R₁ | R₂ | A | phys. data |
|---|---|---|---|---|
| 3.121 | F | Cl | −C(O-CH₂-O)−CH₃ (1,3-dioxolane) | |
| 3.122 | F | Cl | −C(O-CH(CH₃)-CH(CH₃)-O)− (dimethyl dioxolane) | |
| 3.123 | F | Cl | −S−△−COOCH₃ | |
| 3.124 | F | Cl | −S−△−COOC₂H₅ | |
| 3.125 | F | Cl | −S−△−COOC₃H₇ | |
| 3.126 | F | Cl | −S−△−COOCH(CH₃)CH₃ | |
| 3.127 | F | Cl | −S−△−COO−CH₂−CH₂−Cl | |
| 3.128 | F | Cl | −S−△−COOC₅H₁₁ | |
| 3.129 | F | Cl | −S−△−COOCH₂−CH₂−O−CH₃ | |
| 3.130 | F | Cl | −S−△−COOCH(CH₃)−CH₂−S−CH₃ | |
| 3.131 | F | Cl | −S−△−COOCH(CH₃)−N(CH₃)₂ | |
| 3.132 | F | Cl | −S−△−COO−cyclopentyl | |
| 3.133 | F | Cl | −S−△−COO−cyclohexyl | |
| 3.134 | F | Cl | −S−△−COO−CH₂−CH₂−CH=CH₂ | |
| 3.135 | F | Cl | −S−△−COO−CH₂−C(Cl)=CH₂ | |
| 3.136 | F | Cl | −S−△−COO−CH₂−C≡CH | |
| 3.137 | F | Cl | −S−△−COOH | |
| 3.138 | F | Cl | −S−△−CONH₂ | |
| 3.139 | F | Cl | −S−△−CONH−CH₃ | |
| 3.140 | F | Cl | −S−△(CH₃)−COOC₂H₅ | |
| 3.141 | F | Cl | −S−△(C₂H₅)−COOC₂H₅ | |
| 3.142 | F | Cl | −S−△(F)−COOCH₃ | |
| 3.143 | F | Cl | −S−△(F)−COOC₂H₅ | |
| 3.144 | F | Cl | −S−△−COO−CH(CH₃)₂ | |
| 3.145 | F | Cl | −S−△−COO−cyclohexyl | |
| 3.146 | F | Cl | −NH−SO₂−CH₃ | |
| 3.147 | F | Cl | −NH−SO₂−C₂H₅ | |

TABLE 3-continued

Compounds of formula Ie:

(Ie)

| Comp. No. | R₁ | R₂ | A | phys. data |
|---|---|---|---|---|
| 3.148 | F | Cl | —NH—SO₂—Cl | |
| 3.149 | F | Cl | —NH—SO₂—△ (cyclopropyl) | |
| 3.150 | F | Cl | —O—P(=O)(OC₂H₅)(OC₂H₅) | |
| 3.151 | H | Cl | —COOH | |
| 3.152 | H | Cl | —COOCH₃ | |
| 3.153 | H | Cl | —COO—CH(CH₃)₂ | |
| 3.154 | H | Cl | —COO—C₅H₁₁ | |
| 3.155 | H | Cl | —COO—CH₂—CH₂—O—CH₃ | |
| 3.156 | H | Cl | —COOCH₂—S—CH₃ | |
| 3.157 | H | Cl | —COOCH(CH₃)—CH₂—S—CH₃ | |
| 3.158 | H | Cl | —COO—CH(CH₃)—CH₂—N(CH₃)₂ | |
| 3.159 | H | Cl | —CO—N(CH₃)₂ | |
| 3.160 | H | Cl | —CO—N(morpholino) | |
| 3.161 | H | Cl | —COON=C(CH₃)₂ | |
| 3.162 | H | Cl | —COOCH₂—CH₂—O—N=C(CH₃)₂ | |
| 3.163 | H | Cl | —COO—cyclohexyl | |
| 3.164 | H | Cl | —CH—cyclopropyl(CH₃) | |
| 3.165 | H | Cl | —S—C₃H₇ | |
| 3.166 | H | Cl | —COOCH₂—COOCH₃ | |
| 3.167 | H | Cl | —COOCH(CH₃)—COOCH₃ | |
| 3.168 | H | Cl | —COS—CH₂—COOCH₃ | |
| 3.169 | H | Cl | —COS—CH(CH₃)—COOCH₃ | |
| 3.170 | H | Cl | —OH | |
| 3.171 | H | Cl | —OCH₃ | |
| 3.172 | H | Cl | —O—C₂H₅ | |
| 3.173 | H | Cl | —O—CH(CH₃)₂ | |
| 3.174 | H | Cl | —O—CH₂—C≡CH | |
| 3.175 | H | Cl | —O—CH₂—CH=CHCl | |
| 3.176 | H | Cl | —O—CH₂—C(Cl)=CH₂ | |
| 3.177 | H | Cl | —O—CH(CH₃)—C≡CH | |
| 3.178 | H | Cl | —O—CH₂—COOCH₃ | |
| 3.179 | H | Cl | —O—CH₂—COOC₂H₅ | |
| 3.180 | H | Cl | —O—CH(CH₃)—COOCH₃ | |
| 3.181 | H | Cl | —SH | |
| 3.182 | H | Cl | —SCH₃ | |
| 3.183 | H | Cl | —SC₂H₅ | |
| 3.184 | H | Cl | —S—CH(CH₃)₂ | |
| 3.185 | H | Cl | —S—CH₂—COOCH₃ | |
| 3.186 | H | Cl | —S—CH(CH₃)—COOCH₃ | |
| 3.187 | H | Cl | —S—CH₂—COOC₂H₅ | |
| 3.188 | H | Cl | —C(=N—OCH₃)—CN | |
| 3.189 | H | Cl | —C(O—CH(CH₃))₂ (dioxolane with 2 CH₃) | |
| 3.190 | H | Cl | —S—cyclopropyl-COOC₂H₅ | |

TABLE 3-continued

Compounds of formula Ie:

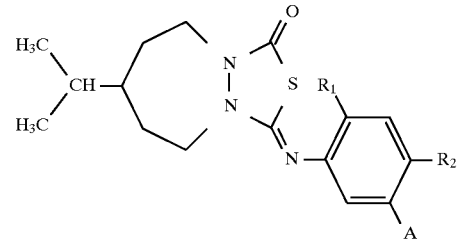

(Ie)

| Comp. No. | R₁ | R₂ | A | phys. data |
|---|---|---|---|---|
| 3.191 | H | Cl | —S—△—COOH | |
| 3.192 | H | Cl | —S—△—COO—CH(CH₃)₂ | |
| 3.193 | H | Cl | —S—△(CH₃)—COOC₂H₅ | |
| 3.194 | H | Cl | —S—△(F)—COOC₂H₅ | |
| 3.195 | H | Cl | —S—△(CF₃)—COOC₂H₅ | |
| 3.196 | H | Cl | —S—△(CF₃)—COO—CH(CH₃)₂ | |
| 3.197 | H | Cl | —S—△—COOH | |
| 3.198 | H | Cl | —S—△(CF₃)—COOH | |
| 3.199 | H | Cl | —S—△(CF₃)—COOC₅H₁₁ | |
| 3.200 | H | Cl | —S—△(C₂H₅)—COOC₂H₅ | |
| 3.201 | H | Cl | —S—△(CH(CH₃)₂)—COOC₂H₅ | |
| 3.202 | H | Cl | —NH—SO₂—C₂H₅ | |
| 3.203 | H | Cl | —NH—SO₂—CH₂—Cl | |
| 3.204 | F | CN | —COOH | |
| 3.205 | F | CN | —COO—CH(CH₃)₂ | |
| 3.206 | F | CN | —O—CH(CH₃)₂ | |
| 3.207 | F | CN | —O—CH₂—C≡CH | |
| 3.208 | F | CN | —O—CH(CH₃)—C≡CH | |
| 3.209 | F | CN | —S—CH₂—COOCH₃ | |
| 3.210 | F | CN | —S—CH(CH₃)—COOCH₃ | |
| 3.211 | F | CN | —O—CH₂—COOCH₃ | |
| 3.212 | F | CN | —O—CH₂—COOC₅H₁₁ | |
| 3.213 | F | CN | —O—CH(CH₃)—COOC₂H₅ | |
| 3.214 | F | CN | —S—△—COOCH₃ | |
| 3.215 | F | CN | —S—△—COOC₂H₅ | |
| 3.216 | F | CN | —S—△(F)—COOC₂H₅ | |
| 3.217 | F | CN | —S—△—COOH | |
| 3.218 | F | CN | —S—△(F)—COOH | |
| 3.219 | F | CN | —S—△(CF₃)—COOH | |
| 3.220 | F | CN | —S—△—COOC₂H₅ | |
| 3.221 | F | Br | —COOH | |

TABLE 3-continued

Compounds of formula Ie:

(Ie)

| Comp. No. | R₁ | R₂ | A | phys. data |
|---|---|---|---|---|
| 3.222 | F | Br | —COO—CH(CH₃)₂ | |
| 3.223 | F | Br | —OH | |
| 3.224 | F | Br | —O—CH(CH₃)₂ | |
| 3.225 | F | Br | —O—CH₂—C≡CH | |
| 3.226 | F | Br | —O—CH(CH₃)—C≡C≡CH | |
| 3.227 | F | Br | —O—CH₂COOCH₃ | |
| 3.228 | F | Br | —O—CH₂—COOC₅H₁₁ | |
| 3.229 | F | Br | S—CH₂—COOCH₃ | |
| 3.230 | F | Br | —S—(cyclopropyl)—COOC₂H₅ | |
| 3.231 | F | Br | —S—(cyclopropyl-F)—COOH | |
| 3.232 | F | Br | —S—(cyclopropyl-F)—COOC₂H₅ | |
| 3.233 | F | Cl | —O—(oxetanyl) | |
| 3.234 | H | Cl | —O—(oxetanyl) | |
| 3.235 | F | Cl | —C(O)—O—(oxetanyl) | |
| 3.236 | H | Cl | —C(O)—O—(oxetanyl) | |

TABLE 4

Compounds of formula If:

(If)

| Comp. No. | R₁ | R₂ | A | phys. data |
|---|---|---|---|---|
| 4.01 | F | Cl | —OH | |
| 4.02 | F | Cl | —O—CH(CH₃)₂ | resin |
| 4.03 | F | Cl | —O—CH₂C≡CH | |
| 4.04 | F | Cl | —O—CH(CH₃)—C≡CH | |
| 4.05 | F | Cl | —S—CH₂—COOC₂H₅ | |
| 4.06 | F | Cl | —O—CH₂—COOCH₃ | |
| 4.07 | F | Cl | —S—CH(CH₃)COOCH₃ | |
| 4.08 | F | Cl | —OCH(CH₃)COOCH₃ | |
| 4.09 | F | Cl | —COOH | |
| 4.10 | F | Cl | —COOCH₃ | $n_D^{22}$ 1.5879 |
| 4.11 | F | Cl | —COO—CH(CH₃)₂ | |
| 4.12 | F | Cl | —S—(cyclopropyl)—COOC₂H₅ | |
| 4.13 | F | Cl | —S—(cyclopropyl-F)—COOC₂H₅ | |
| 4.14 | F | Cl | —S—(cyclopropyl-CF₃)—COOC₂H₅ | |
| 4.15 | H | Cl | —S—CH₂—COOCH₃ | |
| 4.16 | F | Cl | —O—(oxetanyl) | |
| 4.17 | H | Cl | —O—(oxetanyl) | |
| 4.18 | F | Cl | —C(O)—O—(oxetanyl) | |

TABLE 4-continued

Compounds of formula If:

(If)

| Comp. No. | R₁ | R₂ | A | phys. data |
|---|---|---|---|---|
| 4.19 | H | Cl | —C(=O)—O—(oxetanyl) | |

TABLE 5

Compounds of formula Ig (Ig)

| Comp. No. | R₁ | R₂ | A | phys. data |
|---|---|---|---|---|
| 5.01 | F | Cl | —OH | |
| 5.02 | F | Cl | —O—CH(CH₃)₂ | |
| 5.03 | F | Cl | —O—CH₂—C≡CH | |
| 5.04 | F | Cl | —O—CH(CH₃)—C≡CH | |
| 5.05 | F | Cl | —S—CH₂—COOC₂H₅ | |
| 5.06 | F | Cl | —O—CH₂—COOCH₃ | |
| 5.07 | F | Cl | —S—CH(CH₃)COOCH₃ | |
| 5.08 | F | Cl | —OCH(CH₃)COOCH₃ | |
| 5.09 | F | Cl | —COOH | |
| 5.10 | F | Cl | —COOCH₃ | |
| 5.11 | F | Cl | —COO—CH(CH₃)₂ | |
| 5.12 | F | Cl | —S—(cyclopropyl)—COOC₂H₅ | |

TABLE 5-continued

Compounds of formula Ig (Ig)

| Comp. No. | R₁ | R₂ | A | phys. data |
|---|---|---|---|---|
| 5.13 | F | Cl | —S—(cyclopropyl-F)—COOC₂H₅ | |
| 5.14 | F | Cl | —S—(cyclopropyl-CF₃)—COOC₂H₅ | |
| 5.15 | H | Cl | —S—CH₂—COOCH₃ | |
| 5.16 | F | Cl | —O—(oxetanyl) | |
| 5.17 | H | Cl | —O—(oxetanyl) | |
| 5.18 | F | Cl | —C(=O)—O—(oxetanyl) | |
| 5.19 | H | Cl | —C(=O)—O—(oxetanyl) | |

TABLE 6

Compounds of formula Ih (Ih)

| Comp. No. | X₁ | R₁₉ | n₂ | phys. data |
|---|---|---|---|---|
| 6.01 | O | H | 0 | |
| 6.02 | O | H | 1 | |
| 6.03 | O | —CH₃ | 0 | |
| 6.04 | O | —C₂H₅ | 0 | |

TABLE 6-continued

Compounds of formula Ih

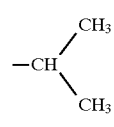

(Ih)

| Comp. No. | $X_1$ | $R_{19}$ | $n_2$ | phys. data |
|---|---|---|---|---|
| 6.05 | O | $-C_2H_5$ | 1 | |
| 6.06 | O | $-CH(CH_3)_2$ | 0 | |
| 6.07 | O | $-CH(CH_3)_2$ | 1 | |
| 6.08 | O | $-CH_2-C\equiv CH$ | 0 | |
| 6.09 | O | $-CH_2-C\equiv CH$ | 1 | |
| 6.10 | O | H | 0 | |
| 6.11 | O | H | 1 | |
| 6.12 | O | $-CH_3$ | 1 | |
| 6.13 | O | $-CH_2-CH=CH_2$ | 0 | |
| 6.14 | O | $-CH_2-CH=CH_2$ | 1 | |
| 6.15 | S | H | 0 | |
| 6.16 | S | $-CH_3$ | 0 | |
| 6.17 | S | $-C_2H_5$ | 0 | |
| 6.18 | S | $-C_3H_7(n)$ | 0 | |
| 6.19 | S | $-CH(CH_3)_2$ | 0 | |
| 6.20 | S | $-C_4H_9(n)$ | 0 | |
| 6.21 | S | $-C_4H_9(s)$ | 0 | |
| 6.22 | S | $-C_4H_9(i)$ | 0 | |
| 6.23 | S | $-C_4H_9(t)$ | 0 | |
| 6.24 | S | $-CH_2-CH=CH_2$ | 0 | |
| 6.25 | S | $-CH_2-CH=CH-CH_3$ | 0 | |
| 6.26 | S | $-CH_2-C(CH_3)=CH_2$ | 0 | |
| 6.27 | S | $-CH_2-C\equiv CH$ | 0 | |
| 6.28 | S | $-CH_2-C\equiv C-CH_3$ | 0 | |
| 6.29 | S | $-CH(CH_3)-C\equiv CH$ | 0 | |
| 6.30 | S | $-CH_2-C(Cl)=CHCl$ | 0 | |
| 6.31 | S | $-CH_2-C(Cl)=CH_2$ | 0 | |
| 6.32 | S | $-CH_2-CH=CHCl$ | 0 | |
| 6.33 | S | $-CH_2-CH=C(Cl)-CH_3$ | 0 | |
| 6.34 | S | $-CH_2-CH=CH-Br$ | 0 | |
| 6.35 | S | $-CH_2-C(Br)=CH-Br$ | 0 | |
| 6.36 | S | $-CH_2-C(Br)=CH_2$ | 0 | |
| 6.37 | S | $-CH_2-O-CH_3$ | 0 | |
| 6.38 | S | $-CH_2-O-C_3H_7$ | 0 | |
| 6.39 | S | $-CH_2-O-C_4H_9$ | 0 | |
| 6.40 | S | $-CH_2-CH_2-O-CH_3$ | 0 | |
| 6.41 | S | $-CH_2-CH_2-O-C_2H_5$ | 0 | |
| 6.42 | S | $-CH_2-CN$ | 0 | |
| 6.43 | S | $-CH_2-CH_2-CN$ | 0 | |
| 6.44 | S | $-CH(CH_3)-CN$ | 0 | |
| 6.45 | S | $-CH_2-COOCH_3$ | 0 | |
| 6.46 | S | $-CH_2-COOC_2H_5$ | 0 | |
| 6.47 | S | $-CH_2-COO-CH(CH_3)_2$ | 0 | |
| 6.48 | S | $-CH_2-COOC_5H_{11}$ | 0 | |
| 6.49 | S | $-CH_2-CH_2-COOCH_3$ | 0 | |
| 6.50 | S | $-CH_2-CH_2-COOC_2H_5$ | 0 | |
| 6.51 | S | $-CH_2-CH_2-COO-CH(CH_3)_2$ | 0 | |
| 6.52 | S | $-CH(CH_3)-COOCH_3$ | 0 | |
| 6.53 | S | $-CH(CH_3)-COOC_2H_5$ | 0 | |
| 6.54 | S | $-CH(CH_3)-COO-CH(CH_3)_2$ | 0 | |
| 6.55 | S | $-CH(CH_3)-COOC_3H_7(n)$ | 0 | |

TABLE 6-continued

Compounds of formula Ih

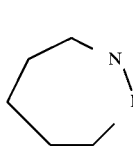

(Ih)

| Comp. No. | X₁ | R₁₉ | n₂ | phys. data |
|---|---|---|---|---|
| 6.56 | S | —CH(CH₃)—COOC₄H₉(n) | 0 | |
| 6.57 | S | —CH(CH₃)—COOC₄H₉(s) | 0 | |
| 6.58 | S | —CH(CH₃)—COOC₄H₉(i) | 0 | |
| 6.59 | S | —CH(CH₃)—COOC₄H₉(t) | 0 | |
| 6.60 | S | —CH(CH₃)—COOC₅H₁₁ | 0 | |
| 6.61 | S | —CH(C₂H₅)—COOCH₃ | 0 | |
| 6.62 | S | —CH(C₂H₅)—COOC₂H₅ | 0 | |
| 6.63 | S | —CH(C₂H₅)—COO—CH(CH₃)CH₃ | 0 | |
| 6.64 | S | —CH₂—cyclohexyl | 0 | |
| 6.65 | S | —CH(CH₃)—cyclopropyl | 0 | |
| 6.66 | S | —CH₂—C₆H₅ | 0 | |
| 6.67 | S | —CH₂—CH₂—N(morpholino, O) | 0 | |
| 6.68 | S | —CH₂—CH₂—N(thiomorpholino, S) | 0 | |
| 6.69 | S | —CH₂—CH₂—N(piperazino)N—CH₃ | 0 | |
| 6.70 | S | —CH(CH₃)—CH₂—N(CH₃)₂ | 0 | |
| 6.71 | S | —CH(CH₃)—C(O)—NH—CH₃ | 0 | |
| 6.72 | S | —CH(CH₃)—C(O)—N(CH₃)₂ | 0 | |
| 6.73 | S | —CH(CH₃)—C(O)—N(CH₃)(C₄H₉) | 0 | |
| 6.74 | S | FCH₂— | 0 | |
| 6.75 | S | F₂CH— | 0 | |
| 6.76 | S | FCH₂—CH₂— | 0 | |
| 6.77 | S | CF₃—CH₂— | 0 | |
| 6.78 | S | FCH₂—CH₂—CH₂— | 0 | |
| 6.79 | S | Cl—CH₂— | 0 | |
| 6.80 | S | Br—CH₂— | 0 | |
| 6.81 | S | Cl₃C— | 0 | |
| 6.82 | S | F₃C— | 0 | |
| 6.83 | S | Cl—CH₂—CH₂— | 0 | |
| 6.84 | S | Br—CH₂—CH₂— | 0 | |
| 6.85 | S | CF₃—CF₂— | 0 | |
| 6.86 | S | IC≡C—CH₂— | 0 | |
| 6.87 | S | CH₃—O—CH₂—O—CH₂— | 0 | |
| 6.88 | S | CH₃—O—CH₂—CH₂—O—CH₂— | 0 | |
| 6.89 | S | C₂H₅—O—CH₂—O—CH₂— | 0 | |
| 6.90 | S | CH₃—O—CH₂—O—CH₂—CH₂— | 0 | |
| 6.91 | S | C₂H₅—O—CH₂—O—CH₂—CH₂— | 0 | |
| 6.92 | S | C₂H₅—O—CH₂—CH₂—O—CH₂— | 0 | |
| 6.93 | S | C₂H₅—O—CH₂—CH₂—O—CH₂—CH₂— | 0 | |
| 6.94 | S | C₆H₅—CH=CH—CH₂— | 0 | |
| 6.95 | S | —CH₂—COOH | 0 | |
| 6.96 | S | —CH(CH₃)—COOH | 0 | |
| 6.97 | S | —CH(C₂H₅)—COOH | 0 | |
| 6.98 | S | —CH₂—CH₂—COOH | 0 | |
| 6.99 | S | Cl—CH₂—CH₂—O—C(O)—CH₂— | 0 | |
| 6.100 | S | F—CH₂—CH₂—O—C(O)—CH₂— | 0 | |

TABLE 6-continued

Compounds of formula Ih

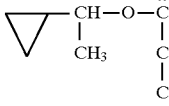

(Ih)

| Comp. No. | X₁ | R₁₉ | n₂ | phys. data |
|---|---|---|---|---|
| 6.101 | S | F—CH₂—CH₂—CH₂—O—C(O)—CH₂— | 0 | |
| 6.102 | S | F₅C₂—CH₂—O—C(O)—CH₂— | 0 | |
| 6.103 | S | Cl—CH₂—CH₂—O—C(O)—CH(CH₃)— | 0 | |
| 6.104 | S | F—CH₂—CH₂—O—C(O)—CH(CH₃)— | 0 | |
| 6.105 | S | F—CH₂—CH₂—CH₂—O—C(O)—CH(CH₃)— | 0 | |
| 6.106 | S | CF₃—CH₂—O—C(O)—CH(CH₃)— | 0 | |
| 6.107 | S | CH₃O—CH₂CH₂—O—C(O)—CH₂— | 0 | |
| 6.108 | S | C₂H₅—O—CH₂—CH₂—O—C(O)—CH₂— | 0 | |
| 6.109 | S | C₃H₇—O—CH₂—CH₂—O—C(O)—CH₂— | 0 | |
| 6.110 | S | C₂H₅—O—C(O)—CH(CH₃)—O—C(O)—CH(CH₃)— | 0 | |
| 6.111 | S | C₂H₅—O—C(O)—CH₂—O—C(O)—CH(CH₃)— | 0 | |
| 6.112 | S | cyclopropyl-CH(CH₃)—O—C(O)—CH(CH₃)— | 0 | |
| 6.113 | S | CH₃—S—CH₂—CH(CH₃)— | 0 | |
| 6.114 | S | C₂H₅—S—CH₂—CH(CH₃)— | 0 | |
| 6.115 | S | CH₃—S—CH₂—CH₂— | 0 | |
| 6.116 | S | C₃H₇—S—CH₂—CH(CH₃)— | 0 | |
| 6.117 | S | (CH₃)₂CH—S—CH₂—CH(CH₃)— | 0 | |
| 6.118 | S | C₄H₉—S—CH₂—CH(CH₃)— | 0 | |
| 6.119 | S | C₅H₁₁—S—CH₂—CH(CH₃)— | 0 | |
| 6.120 | S | CH₃—SO₂— | 0 | |
| 6.121 | S | C₂H₅SO₂— | 0 | |
| 6.122 | S | CH₂=CH—CH₂—O—CH₂— | 0 | |
| 6.123 | S | oxetanyl(CH₃)—CH₂— | 0 | |
| 6.124 | S | oxetanyl-O—C(O)—CH(CH₃)— | 0 | |
| 6.125 | S | thietanyl-O—C(O)—CH(CH₃)— | 0 | |
| 6.126 | S | C₂H₅—S—C(O)—CH(CH₃)— | 0 | |
| 6.127 | S | H₇C₃—S—C(O)—CH(CH₃)—O—C(O)—CH(CH₃)— | 0 | |
| 6.128 | S | CH₃—O—C(O)—C(CH₃)(O)—OC(O)—CH(CH₃)— | 0 | |

TABLE 7

Compounds of formula Ii

![structure Ii]

| Comp. No. | R | $R_{23}$ | phys. data |
|---|---|---|---|
| 7.01 | H | F | |
| 7.02 | H | H | |
| 7.03 | —CH$_3$ | F | |
| 7.04 | —CH$_3$ | H | |
| 7.05 | —C$_2$H$_5$ | F | |
| 7.06 | —C$_2$H$_5$ | H | |
| 7.07 | —CH(CH$_3$)$_2$ | F | |
| 7.08 | —CH(CH$_3$)$_2$ | H | |
| 7.09 | —CF$_3$ | F | |
| 7.10 | —CF$_3$ | H | |

TABLE 8

Compounds of formula Ij

![structure Ij] (Ij)

| Comp. No. | R | $R_{24}$ | $R_{25}$ | $R_{26}$ | phys. data |
|---|---|---|---|---|---|
| 8.01 | H | H | H | H | |
| 8.02 | H | F | H | H | |
| 8.03 | H | F | —CH$_3$ | H | |
| 8.04 | H | F | —CH$_3$ | —CH$_3$ | |
| 8.05 | H | F | —CH(CH$_3$)$_2$ | H | |
| 8.06 | H | F | —CH(CH$_3$)$_2$ | —CH$_3$ | |
| 8.07 | H | F | —CH$_2$—C≡CH | —CH$_3$ | |
| 8.08 | —CH$_3$ | F | —CH$_2$—C≡CH | H | |
| 8.09 | —CH$_3$ | F | —CH$_2$—C≡CH | —CH$_3$ | |

TABLE 8-continued

Compounds of formula Ij

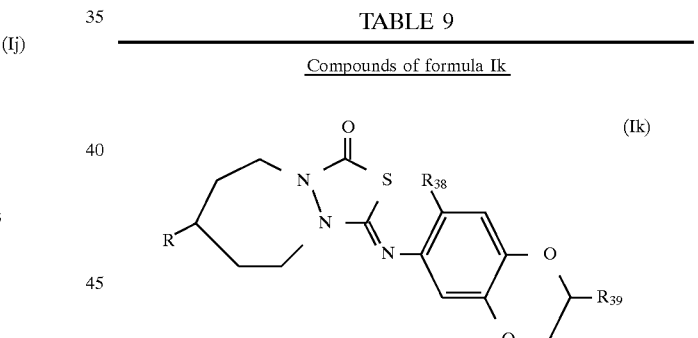

| Comp. No. | R | $R_{24}$ | $R_{25}$ | $R_{26}$ | phys. data |
|---|---|---|---|---|---|
| 8.10 | —CH(CH$_3$)$_2$ | F | —CH$_2$—C≡CH | H | |
| 8.11 | —CH(CH$_3$)$_2$ | F | —CH$_2$—C≡CH | —CH$_3$ | |
| 8.12 | —CF$_3$ | F | —CH$_2$—C≡CH | H | |
| 8.13 | —CF$_3$ | F | —CH$_2$—C≡CH | —CH$_3$ | |

TABLE 9

Compounds of formula Ik

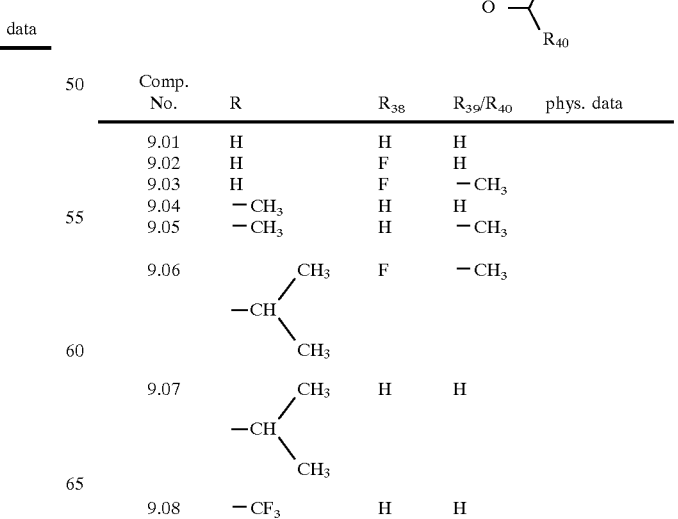

| Comp. No. | R | $R_{38}$ | $R_{39}/R_{40}$ | phys. data |
|---|---|---|---|---|
| 9.01 | H | H | H | |
| 9.02 | H | F | H | |
| 9.03 | H | F | —CH$_3$ | |
| 9.04 | —CH$_3$ | H | H | |
| 9.05 | —CH$_3$ | H | —CH$_3$ | |
| 9.06 | —CH(CH$_3$)$_2$ | F | —CH$_3$ | |
| 9.07 | —CH(CH$_3$)$_2$ | H | H | |
| 9.08 | —CF$_3$ | H | H | |

TABLE 9-continued

Compounds of formula Ik (Ik)

| Comp. No. | R | $R_{38}$ | $R_{39}/R_{40}$ | phys. data |
|---|---|---|---|---|
| 9.09 | —$CF_3$ | F | —$CH_3$ | |

TABLE 10

Compounds of formula Il (Il)

| Comp. No. | R | $R_{41}$ | $R_{32}$ | phys. data |
|---|---|---|---|---|
| 10.01 | H | H | H | |
| 10.02 | H | F | H | |
| 10.03 | H | F | —$CH_3$ | |
| 10.04 | —$CH_3$ | H | H | |
| 10.05 | —$CH_3$ | F | H | |
| 10.06 | —$CH_3$ | F | —$CH_3$ | |
| 10.07 | —CH(CH$_3$)$_2$ | H | H | |
| 10.08 | —CH(CH$_3$)$_2$ | F | H | |
| 10.09 | —CH(CH$_3$)$_2$ | F | —$CH_3$ | |
| 10.10 | —$CF_3$ | H | H | |
| 10.11 | —$CF_3$ | F | H | |
| 10.12 | —$CF_3$ | F | —$CH_3$ | |

TABLE 11

Compounds of formula Im (Im)

| Comp. No. | R | $R_{27}$ | $R_{29}$ | $R_{28}$ | phys. data |
|---|---|---|---|---|---|
| 11.01 | H | H | H | H | |
| 11.02 | H | F | H | H | |
| 11.03 | H | F | —$CH_3$ | H | |
| 11.04 | —$CH_3$ | F | —$CH_3$ | H | |
| 11.05 | —$CH_3$ | F | —$CH_2$—C≡CH | H | |
| 11.06 | H | F | —$CH_2$—C≡CH | H | |
| 11.07 | —CH(CH$_3$)$_2$ | F | —$CH_2$—C≡CH | H | |
| 11.08 | —$CF_3$ | F | —$CH_2$—C≡CH | H | |
| 11.09 | —$CF_3$ | F | —$CH_2$—C≡CH | —$CH_3$ | |
| 11.10 | H | H | —$CH_2$—C≡CH | —$CH_3$ | |
| 11.11 | H | F | —$CH_2$—C≡CH | —$CH_3$ | |

TABLE 12

Compounds of formula In (In)

| Comp. No. | R | $R_{37}$ | $R_{36}$ | phys. data |
|---|---|---|---|---|
| 12.01 | H | H | H | |
| 12.02 | H | F | H | |
| 12.03 | H | F | —$CH_3$ | |
| 12.04 | H | F | —$CH_2$—C≡CH | |
| 12.05 | H | F | —CH(CH$_3$)$_2$ | |

TABLE 12-continued

Compounds of formula In (In)

| Comp. No. | R | $R_{37}$ | $R_{36}$ | phys. data |
|---|---|---|---|---|
| 12.06 | $-CF_3$ | F | $-CH_2-C{\equiv}CH$ | |

TABLE 13

Compounds of formula Io (Io)

| Comp. No. | R | $R_{33}$ | $R_{34}$ | $R_{35}$ | phys. data |
|---|---|---|---|---|---|
| 13.01 | H | H | H | H | |
| 13.02 | H | H | $-CH_3$ | H | |
| 13.03 | H | H | $-CH_2-C{\equiv}CH$ | H | |
| 13.04 | H | F | H | H | |
| 13.05 | H | F | $-CH_3$ | H | |
| 13.06 | H | F | $-CH_2-C{\equiv}CH$ | H | |
| 13.07 | $-CF_3$ | F | $-CH_2-C{\equiv}CH$ | H | |

TABLE 14

Compounds of formula Ip (Ip)

| Comp. No. | R | $R_{30}$ | $R_{31}$ | phys. data |
|---|---|---|---|---|
| 14.01 | H | H | H | |
| 14.02 | H | F | H | |
| 14.03 | H | F | $-CH_3$ | |
| 14.04 | H | F | $-CH(CH_3)_2$ | |
| 14.05 | H | F | $-CH_2-C{\equiv}CH$ | |
| 14.06 | $-CH_3$ | F | $-O-CH_2-C{\equiv}CH$ | |
| 14.07 | $-CH(CH_3)_2$ | F | $-O-CH_2-C{\equiv}CH$ | |

TABLE 15

Compounds of formula Iq (Iq)

| Comp. No. | $X_1$ | $R_{19}$ | $n_2$ | phys. data |
|---|---|---|---|---|
| 15.01 | O | H | 0 | |
| 15.02 | O | H | 1 | |
| 15.03 | O | $-CH_3$ | 0 | |
| 15.04 | O | $-C_2H_5$ | 0 | |
| 15.05 | O | $-C_2H_5$ | 1 | |
| 15.06 | O | $-CH(CH_3)_2$ | 0 | |

TABLE 15-continued

Compounds of formula Iq

| Comp. No. | X$_1$ | R$_{19}$ | n$_2$ | phys. data |
|---|---|---|---|---|
| 15.07 | O | —CH(CH$_3$)$_2$ | 1 | |
| 15.08 | O | —CH$_2$—C≡CH | 0 | |
| 15.09 | O | —CH$_2$—C≡CH | 1 | |
| 15.10 | O | H | 0 | |
| 15.11 | O | H | 1 | |
| 15.12 | O | —CH$_3$ | 1 | |
| 15.13 | O | —CH$_2$—CH=CH$_2$ | 0 | |
| 15.14 | O | —CH$_2$—CH=CH$_2$ | 1 | |
| 15.15 | S | H | 0 | |
| 15.16 | S | —CH$_3$ | 0 | |
| 15.17 | S | —C$_2$H$_5$ | 0 | |
| 15.18 | S | —C$_3$H$_7$(n) | 0 | |
| 15.19 | S | —CH(CH$_3$)$_2$ | 0 | |
| 15.20 | S | —C$_4$H$_9$(n) | 0 | |
| 15.21 | S | —C$_4$H$_9$(s) | 0 | |
| 15.22 | S | —C$_4$H$_9$(i) | 0 | |
| 15.23 | S | —C$_4$H$_9$(t) | 0 | |
| 15.24 | S | —CH$_2$—CH=CH$_2$ | 0 | |
| 15.25 | S | —CH$_2$—CH=CH—CH$_3$ | 0 | |
| 15.26 | S | —CH$_2$—C(CH$_3$)=CH$_2$ | 0 | |
| 15.27 | S | —CH$_2$—C≡CH | 0 | |
| 15.28 | S | —CH$_2$—C≡C—CH$_3$ | 0 | |
| 15.29 | S | —CH(CH$_3$)—C≡CH | 0 | |
| 15.30 | S | —CH$_2$—C(Cl)=CHCl | 0 | |
| 15.31 | S | —CH$_2$—C(Cl)=CH$_2$ | 0 | |
| 15.32 | S | —CH$_2$—CH=CHCl | 0 | |
| 15.33 | S | —CH$_2$—CH=C(Cl)—CH$_3$ | 0 | |
| 15.34 | S | —CH$_2$—CH=CH—Br | 0 | |
| 15.35 | S | —CH$_2$—C(Br)=CH—Br | 0 | |
| 15.36 | S | —CH$_2$—C(Br)=CH$_2$ | 0 | |
| 15.37 | S | —CH$_2$—O—CH$_3$ | 0 | |
| 15.38 | S | —CH$_2$—O—C$_3$H$_7$ | 0 | |
| 15.39 | S | —CH$_2$—O—C$_4$H$_9$ | 0 | |
| 15.40 | S | —CH$_2$—CH$_2$—O—CH$_3$ | 0 | |
| 15.41 | S | —CH$_2$—CH$_2$—O—C$_2$H$_5$ | 0 | |
| 15.42 | S | —CH$_2$—CN | 0 | |
| 15.43 | S | —CH$_2$—CH$_2$—CN | 0 | |
| 15.44 | S | —CH(CH$_3$)—CN | 0 | |
| 15.45 | S | —CH$_2$—COOCH$_3$ | 0 | |
| 15.46 | S | —CH$_2$—COOC$_2$H$_5$ | 0 | |
| 15.47 | S | —CH$_2$—COO—CH(CH$_3$)$_2$ | 0 | |
| 15.48 | S | —CH$_2$—COOC$_5$H$_{11}$ | 0 | |
| 15.49 | S | —CH$_2$—CH$_2$—COOCH$_3$ | 0 | |
| 15.50 | S | —CH$_2$—CH$_2$—COOC$_2$H$_5$ | 0 | |
| 15.51 | S | —CH$_2$—CH$_2$—COO—CH(CH$_3$)$_2$ | 0 | |
| 15.52 | S | —CH(CH$_3$)—COOCH$_3$ | 0 | |
| 15.53 | S | —CH(CH$_3$)—COOC$_2$H$_5$ | 0 | |
| 15.54 | S | —CH(CH$_3$)—COO—CH(CH$_3$)$_2$ | 0 | |
| 15.55 | S | —CH(CH$_3$)—COOC$_3$H$_7$(n) | 0 | |
| 15.56 | S | —CH(CH$_3$)—COOC$_4$H$_9$(n) | 0 | |

TABLE 15-continued

Compounds of formula Iq

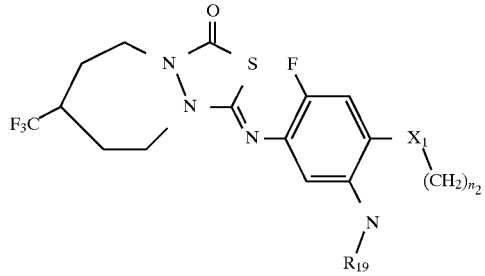
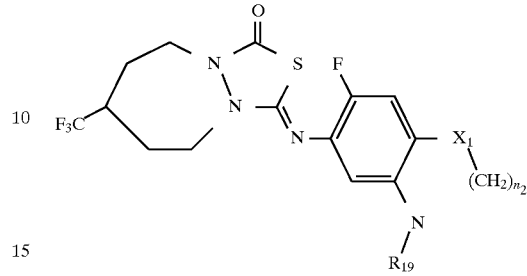

| Comp. No. | $X_1$ | $R_{19}$ | $n_2$ | phys. data |
|---|---|---|---|---|
| 15.57 | S | —CH(CH$_3$)—COOC$_4$H$_9$(s) | 0 | |
| 15.58 | S | —CH(CH$_3$)—COOC$_4$H$_9$(i) | 0 | |
| 15.59 | S | —CH(CH$_3$)—COOC$_4$H$_9$(t) | 0 | |
| 15.60 | S | —CH(CH$_3$)—COOC$_5$H$_{11}$ | 0 | |
| 15.61 | S | —CH(C$_2$H$_5$)—COOCH$_3$ | 0 | |
| 15.62 | S | —CH(C$_2$H$_5$)—COOC$_2$H$_5$ | 0 | |
| 15.63 | S | —CH(C$_2$H$_5$)—COO—CH(CH$_3$)$_2$ | 0 | |
| 15.64 | S | —CH$_2$—C$_6$H$_{11}$ | 0 | |
| 15.65 | S | —CH(CH$_3$)—cyclopropyl | 0 | |
| 15.66 | S | —CH$_2$—C$_6$H$_5$ | 0 | |
| 15.67 | S | —CH$_2$—CH$_2$—N(morpholino, O) | 0 | |
| 15.68 | S | —CH$_2$—CH$_2$—N(thiomorpholino, S) | 0 | |
| 15.69 | S | —CH$_2$—CH$_2$—N(piperazino, N—CH$_3$) | 0 | |
| 15.70 | S | S—CH(CH$_3$)—CH$_2$—N(CH$_3$)$_2$ | 0 | |
| 15.71 | S | —CH(CH$_3$)—C(O)—NH—CH$_3$ | 0 | |
| 15.72 | S | —CH(CH$_3$)—C(O)—N(CH$_3$)$_2$ | 0 | |
| 15.73 | S | —CH(CH$_3$)—C(O)—N(CH$_3$)(C$_4$H$_9$) | 0 | |
| 15.74 | S | FCH$_2$— | 0 | |
| 15.75 | S | F$_2$CH— | 0 | |
| 15.76 | S | FCH$_2$—CH$_2$— | 0 | |
| 15.77 | S | CF$_3$—CH$_2$— | 0 | |
| 15.78 | S | FCH$_2$—CH$_2$—CH$_2$— | 0 | |
| 15.79 | S | Cl—CH$_2$— | 0 | |
| 15.80 | S | Br—CH$_2$— | 0 | |
| 15.81 | S | Cl$_3$C— | 0 | |
| 15.82 | S | F$_3$C— | 0 | |
| 15.83 | S | Cl—CH$_2$—CH$_2$— | 0 | |
| 15.84 | S | Br—CH$_2$—CH$_2$— | 0 | |
| 15.85 | S | CF$_3$—CF$_2$— | 0 | |
| 15.86 | S | IC≡C—CH$_2$— | 0 | |
| 15.87 | S | CH$_3$—O—CH$_2$—O—CH$_2$— | 0 | |
| 15.88 | S | CH$_3$—O—CH$_2$—CH$_2$—O—CH$_2$— | 0 | |
| 15.89 | S | C$_2$H$_5$—O—CH$_2$—O—CH$_2$— | 0 | |
| 15.90 | S | CH$_3$—O—CH$_2$—O—CH$_2$—CH$_2$— | 0 | |
| 15.91 | S | C$_2$H$_5$—O—CH$_2$—O—CH$_2$—CH$_2$— | 0 | |
| 15.92 | S | C$_2$H$_5$—O—CH$_2$—CH$_2$—O—CH$_2$— | 0 | |
| 15.93 | S | C$_2$H$_5$—O—CH$_2$—CH$_2$—O—CH$_2$—CH$_2$— | 0 | |
| 15.94 | S | C$_6$H$_5$—CH=CH—CH$_2$— | 0 | |
| 15.95 | S | —CH$_2$—COOH | 0 | |
| 15.96 | S | —CH(CH$_3$)—COOH | 0 | |
| 15.97 | S | —CH(C$_2$H$_5$)—COOH | 0 | |
| 15.98 | S | —CH$_2$—CH$_2$—COOH | 0 | |
| 15.99 | S | Cl—CH$_2$—CH$_2$—O—C(O)—CH$_2$— | 0 | |
| 15.100 | S | F—CH$_2$—CH$_2$—O—C(O)—CH$_2$— | 0 | |

TABLE 15-continued

Compounds of formula Iq

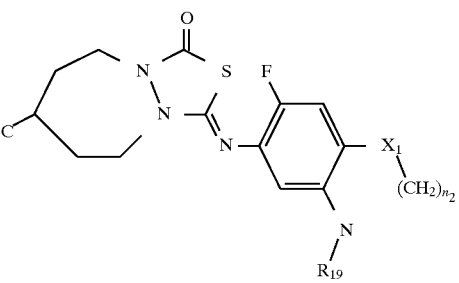

| Comp. No. | X₁ | R₁₉ | n₂ | phys. data |
|---|---|---|---|---|
| 15.101 | S | F—CH₂—CH₂—CH₂—O—C(O)—CH₂— | 0 | |
| 15.102 | S | F₅C₂—CH₂—O—C(O)—CH₂— | 0 | |
| 15.103 | S | Cl—CH₂—CH₂—O—C(O)—CH(CH₃)— | 0 | |
| 15.104 | S | F—CH₂—CH₂—O—C(O)—CH(CH₃)— | 0 | |
| 15.105 | S | F—CH₂—CH₂—CH₂—O—C(O)—CH(CH₃)— | 0 | |
| 15.106 | S | CF₃—CH₂—O—C(O)—CH(CH₃)— | 0 | |
| 15.107 | S | CH₃—O—CH₂—CH₂—O—C(O)—CH₂— | 0 | |
| 15.108 | S | C₂H₅—O—CH₂—CH₂—O—C(O)—CH₂— | 0 | |
| 15.109 | S | C₃H₇—O—CH₂—CH₂—O—C(O)—CH₂— | 0 | |
| 15.110 | S | C₂H₅—O—C(O)—CH(CH₃)—O—C(O)—CH(CH₃)— | 0 | |
| 15.111 | S | C₂H₅—O—C(O)—CH₂—O—C(O)—CH(CH₃)— | 0 | |
| 15.112 | S | cyclopropyl-CH(CH₃)—O—C(O)—CH(CH₃)— | 0 | |
| 15.113 | S | CH₃—S—CH₂—CH(CH₃)— | 0 | |
| 15.114 | S | C₂H₅—S—CH₂—CH(CH₃)— | 0 | |
| 15.115 | S | CH₃—S—CH₂—CH₂— | 0 | |
| 15.116 | S | C₃H₇—S—CH₂—CH(CH₃)— | 0 | |
| 15.117 | S | (CH₃)₂CH—S—CH₂—CH(CH₃)— | 0 | |
| 15.118 | S | C₄H₉—S—CH₂—CH(CH₃)— | 0 | |
| 15.119 | S | C₅H₁₁—S—CH₂—CH(CH₃)— | 0 | |
| 15.120 | S | CH₃—SO₂— | 0 | |
| 15.121 | S | C₂H₅SO₂— | 0 | |
| 15.122 | S | CH₂=CH—CH₂—O—CH₂— | 0 | |
| 15.123 | S | oxetanyl(CH₃)—CH₂— | 0 | |
| 15.124 | S | oxetanyl-O—C(O)—CH(CH₃)— | 0 | |
| 15.125 | S | thietanyl-O—C(O)—CH(CH₃)— | 0 | |
| 15.126 | S | C₂H₅—S—C(O)—CH(CH₃)— | 0 | |
| 15.127 | S | H₇C₃—S—C(O)—C(CH₃)—O—C(O)—CH(CH₃)— | 0 | |
| 15.128 | S | CH₃—O—C(=O)—C(CH₃)—O—C(O)—CH(CH₃)— | 0 | |

TABLE 16

Compounds of formula Ir

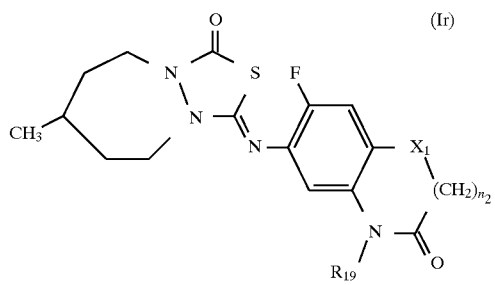

| Comp. No. | $X_1$ | $R_{19}$ | $n_2$ | phys. data |
|---|---|---|---|---|
| 16.01 | O | H | 0 | |
| 16.02 | O | H | 1 | |
| 16.03 | O | —CH$_3$ | 0 | |
| 16.04 | O | —C$_2$H$_5$ | 0 | |
| 16.05 | O | —C$_2$H$_5$ | 1 | |
| 16.06 | O | —CH(CH$_3$)$_2$ | 0 | |
| 16.07 | O | —CH(CH$_3$)$_2$ | 1 | |
| 16.08 | O | —CH$_2$—C≡CH | 0 | |
| 16.09 | O | —CH$_2$—C≡CH | 1 | |
| 16.10 | O | H | 0 | |
| 16.11 | O | H | 1 | |
| 16.12 | O | —CH$_3$ | 1 | |
| 16.13 | O | —CH$_2$—CH=CH$_2$ | 0 | |
| 16.14 | O | —CH$_2$—CH=CH$_2$ | 1 | |
| 16.15 | S | H | 0 | |
| 16.16 | S | —CH$_3$ | 0 | |
| 16.17 | S | —C$_2$H$_5$ | 0 | |
| 16.18 | S | —C$_3$H$_7$(n) | 0 | |
| 16.19 | S | —CH(CH$_3$)$_2$ | 0 | |
| 16.20 | S | —C$_4$H$_9$(n) | 0 | |
| 16.21 | S | —C$_4$H$_9$(s) | 0 | |
| 16.22 | S | —C$_4$H$_9$(i) | 0 | |
| 16.23 | S | —C$_4$H$_9$(t) | 0 | |
| 16.24 | S | —CH$_2$—CH=CH$_2$ | 0 | |
| 16.25 | s | —CH$_2$—CH=CH—CH$_3$ | 0 | |
| 16.26 | S | —CH$_2$—C(CH$_3$)=CH$_2$ | 0 | |
| 16.27 | S | —CH$_2$—C≡CH | 0 | |
| 16.28 | S | —CH$_2$—C≡C—CH$_3$ | 0 | |
| 16.29 | S | —CH(CH$_3$)—C≡CH | 0 | |
| 16.30 | S | —CH$_2$—C(Cl)=CHCl | 0 | |
| 16.31 | S | —CH$_2$—C(Cl)=CH$_2$ | 0 | |
| 16.32 | S | —CH$_2$—CH=CHCl | 0 | |
| 16.33 | S | —CH$_2$—CH=C(Cl)—CH$_3$ | 0 | |
| 16.34 | S | —CH$_2$—CH=CH—Br | 0 | |
| 16.35 | S | —CH$_2$—C(Br)=CH—Br | 0 | |
| 16.36 | S | —CH$_2$—C(Br)=CH$_2$ | 0 | |
| 16.37 | S | —CH$_2$—O—CH$_3$ | 0 | |
| 16.38 | S | —CH$_2$—O—C$_3$H$_7$ | 0 | |
| 16.39 | S | —CH$_2$—O—C$_4$H$_9$ | 0 | |
| 16.40 | S | —CH$_2$—CH$_2$—O—CH$_3$ | 0 | |
| 16.41 | S | —CH$_2$—CH$_2$—O—C$_2$H$_5$ | 0 | |
| 16.42 | S | —CH$_2$—CN | 0 | |
| 16.43 | S | —CH$_2$—CH$_2$—CN | 0 | |
| 16.44 | S | —CH(CH$_3$)—CN | 0 | |
| 16.45 | S | —CH$_2$—COOCH$_3$ | 0 | |
| 16.46 | S | —CH$_2$—COOC$_2$H$_5$ | 0 | |
| 16.47 | S | —CH$_2$—COO—CH(CH$_3$)$_2$ | 0 | |
| 16.48 | S | —CH$_2$—COOC$_5$H$_{11}$ | 0 | |
| 16.49 | S | —CH$_2$—CH$_2$—COOCH$_3$ | 0 | |
| 16.50 | S | —CH$_2$—CH$_2$—COOC$_2$H$_5$ | 0 | |
| 16.51 | S | —CH$_2$—CH$_2$—COO—CH(CH$_3$)$_2$ | 0 | |
| 16.52 | S | —CH(CH$_3$)—COOCH$_3$ | 0 | |
| 16.53 | S | —CH(CH$_3$)—COOC$_2$H$_5$ | 0 | |

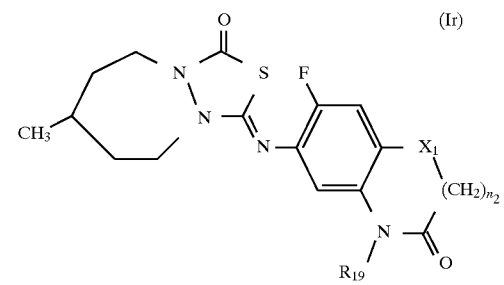

TABLE 16-continued

Compounds of formula Ir (Ir)

| Comp. No. | $X_1$ | $R_{19}$ | $n_2$ | phys. data |
|---|---|---|---|---|
| 16.54 | S | —CH(CH$_3$)—COO—CH(CH$_3$)$_2$ | 0 | |
| 16.55 | S | —CH(CH$_3$)—COOC$_3$H$_7$(n) | 0 | |
| 16.56 | S | —CH(CH$_3$)—COOC$_4$H$_9$(n) | 0 | |
| 16.57 | S | —CH(CH$_3$)—COOC$_4$H$_9$(s) | 0 | |
| 16.58 | S | —CH(CH$_3$)—COOC$_4$H$_9$(i) | 0 | |
| 16.59 | S | —CH(CH$_3$)—COOC$_4$H$_9$(t) | 0 | |
| 16.60 | S | —CH(CH$_3$)—COOC$_5$H$_{11}$ | 0 | |
| 16.61 | S | —CH(C$_2$H$_5$)—COOCH$_3$ | 0 | |
| 16.62 | S | —CH(C$_2$H$_5$)—COOC$_2$H$_5$ | 0 | |
| 16.63 | S | —CH(C$_2$H$_5$)—COO—CH(CH$_3$)$_2$ | 0 | |
| 16.64 | S | —CH$_2$—cyclohexyl | 0 | |
| 16.65 | S | —CH(CH$_3$)—cyclopropyl | 0 | |
| 16.66 | S | —CH$_2$—phenyl | 0 | |
| 16.67 | S | —CH$_2$—CH$_2$—N(morpholino) | 0 | |
| 16.68 | S | —CH$_2$—CH$_2$—N(thiomorpholino) | 0 | |
| 16.69 | S | —CH$_2$—CH$_2$—N(4-methylpiperazino) | 0 | |
| 16.70 | S | —CH(CH$_3$)—CH$_2$—N(CH$_3$)$_2$ | 0 | |
| 16.71 | S | —CH(CH$_3$)—C(O)—NH—CH$_3$ | 0 | |
| 16.72 | S | —CH(CH$_3$)—C(O)—N(CH$_3$)$_2$ | 0 | |
| 16.73 | S | —CH(CH$_3$)—C(O)—N(CH$_3$)(C$_4$H$_9$) | 0 | |
| 16.74 | S | FCH$_2$— | 0 | |
| 16.75 | S | F$_2$CH— | 0 | |
| 16.76 | S | FCH$_2$—CH$_2$— | 0 | |
| 16.77 | S | CF$_3$—CH$_2$— | 0 | |
| 16.78 | S | FCH$_2$—CH$_2$—CH$_2$— | 0 | |
| 16.79 | S | Cl—CH$_2$— | 0 | |
| 16.80 | S | Br—CH$_2$— | 0 | |
| 16.81 | S | Cl$_3$C— | 0 | |
| 16.82 | S | F$_3$C— | 0 | |
| 16.83 | S | Cl—CH$_2$—CH$_2$— | 0 | |
| 16.84 | S | Br—CH$_2$—CH$_2$— | 0 | |
| 16.85 | S | CF$_3$—CF$_2$— | 0 | |
| 16.86 | S | IC≡C—CH$_2$— | 0 | |
| 16.87 | S | CH$_3$—O—CH$_2$—O—CH$_2$— | 0 | |
| 16.88 | S | CH$_3$—O—CH$_2$—CH$_2$—O—CH$_2$— | 0 | |
| 16.89 | S | C$_2$H$_5$—O—CH$_2$—O—CH$_2$— | 0 | |
| 16.90 | S | CH$_3$—O—CH$_2$—O—CH$_2$—CH$_2$— | 0 | |
| 16.91 | S | C$_2$H$_5$—O—CH$_2$—O—CH$_2$—CH$_2$— | 0 | |
| 16.92 | S | C$_2$H$_5$—O—CH$_2$—CH$_2$—O—CH$_2$— | 0 | |
| 16.93 | S | C$_2$H$_5$—O—CH$_2$—CH$_2$—O—CH$_2$—CH$_2$— | 0 | |
| 16.94 | S | C$_6$H$_5$—CH=CH—CH$_2$— | 0 | |
| 16.95 | S | —CH$_2$—COOH | 0 | |

TABLE 16-continued

Compounds of formula Ir (Ir)

| Comp. No. | X₁ | R₁₉ | n₂ | phys. data |
|---|---|---|---|---|
| 16.96 | S | —CH(CH₃)—COOH | 0 | |
| 16.97 | S | —CH(C₂H₅)—COOH | 0 | |
| 16.98 | S | —CH₂—CH₂—COOH | 0 | |
| 16.99 | S | Cl—CH₂—CH₂—O—C(O)—CH₂— | 0 | |
| 16.100 | S | F—CH₂—CH₂—O—C(O)—CH₂— | 0 | |
| 16.101 | S | F—CH₂—CH₂—CH₂—O—C(O)—CH₂— | 0 | |
| 16.102 | S | F₅C₂—CH₂—O—C(O)—CH₂— | 0 | |
| 16.103 | S | Cl—CH₂—CH₂—O—C(O)—CH(CH₃)— | 0 | |
| 16.104 | S | F—CH₂—CH₂—O—C(O)—CH(CH₃)— | 0 | |
| 16.105 | S | F—CH₂—CH₂—CH₂—O—C(O)—CH(CH₃)— | 0 | |
| 16.106 | S | CF₃—CH₂—O—C(O)—CH(CH₃)— | 0 | |
| 16.107 | S | CH₃—O—CH₂—CH₂—O—C(O)—CH₂ | 0 | |
| 16.108 | S | C₂H₅—O—CH₂—CH₂—O—C(O)—CH₂— | 0 | |
| 16.109 | S | C₃H₇—O—CH₂—CH₂—O—C(O)—CH₂— | 0 | |
| 16.110 | S | C₂H₅—O—C(O)—CH(CH₃)—O—C(O)—CH(CH₃)— | 0 | |
| 16.111 | S | C₂H₅—O—C(O)—CH₂—O—C(O)—C(CH₃)(CH₃)— | 0 | |
| 16.112 | S | cyclopropyl-CH(CH₃)—O—C(O)—CH(CH₃)— | 0 | |
| 16.113 | S | CH₃—S—CH₂—CH(CH₃)— | 0 | |
| 16.114 | S | C₂H₅—S—CH₂—CH(CH₃)— | 0 | |
| 16.115 | S | CH₃—S—CH₂—CH₂— | 0 | |
| 16.116 | S | C₃H₇—S—CH₂—CH(CH₃)— | 0 | |
| 16.117 | S | (CH₃)₂CH—S—CH₂—CH(CH₃)— | 0 | |
| 16.118 | S | C₄H₉—S—CH₂—CH(CH₃)— | 0 | |
| 16.119 | S | C₅H₁₁—S—CH₂—CH(CH₃)— | 0 | |
| 16.120 | S | CH₃—SO₂— | 0 | |
| 16.121 | S | C₂H₅SO₂— | 0 | |
| 16.122 | S | CH₂=CH—CH₂—O—CH₂ | 0 | |
| 16.123 | S | oxetanyl-C(CH₃)(CH₂—) | 0 | |
| 16.124 | S | oxetanyl-O—C(O)—CH(CH₃)— | 0 | |
| 16.125 | S | thietanyl-O—C(O)—CH(CH₃)— | 0 | |
| 16.126 | S | C₂H₅—S—C(O)—CH(CH₃)— | 0 | |

TABLE 16-continued

Compounds of formula Ir (Ir)

[Chemical structure: azepane ring with N-N, C=S group, connected to fluorophenyl with $X_1$, $(CH_2)_{n_2}$, and N-$R_{19}$-C=O group; methyl on azepane]

| Comp. No. | $X_1$ | $R_{19}$ | $n_2$ | phys. data |
|---|---|---|---|---|
| 16.127 | S | $H_7C_3-S-\overset{O}{\underset{\|}{C}}-\overset{CH_3}{\underset{\|}{C}}H-O-\overset{O}{\underset{\|}{C}}-\overset{CH_3}{\underset{\|}{C}H}-CH_3$ | 0 | |
| 16.128 | S | $CH_3-O-\overset{O}{\underset{\|}{C}}-\overset{CH_3}{\underset{\|}{C}}-O-\overset{O}{\underset{\|}{C}}-\overset{CH_3}{\underset{\|}{C}H}-CH_3$ | 0 | |

Formulation examples for compounds of formula I (throughout, percentages are by weight)

F1. Emulsifiable concentrates

| | a) | b) | c) | d) |
|---|---|---|---|---|
| a compound of Tables 1-16 | 5% | 10% | 24% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| aromatic hydrocarbon mixture $C_9$–$C_{12}$ | 85% | 78% | 55% | 16% |

Emulsions of any desired concentration can be produced from such concentrates by dilution with water.

F2. Solutions

| | a) | b) | c) | d) |
|---|---|---|---|---|
| a compound of Tables 1–16 | 5% | 10% | 50% | 90% |
| dipropylene glycol methyl ether | — | 20% | 20% | — |
| polyethylene glycol mol. wt. 400 | 20% | 10% | — | — |
| N-methyl-2-pyrrolidone | — | — | 30% | 10% |
| aromatic hydrocarbon mixture $C_9$–$C_{12}$ | 75% | 60% | — | — |

These solutions are suitable for application in the form of micro-drops.

F3. Wettable powders

| | a) | b) | c) | d) |
|---|---|---|---|---|
| a compound of Tables 1–16 | 5% | 25% | 50% | 80% |
| sodium lignosulfonate | 4% | — | 3% | — |
| sodium lauryl sulfate | 2% | 3% | — | 4% |
| sodium diisobutylnaphthalene sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, affording wettable powders which can be diluted with water to give suspensions of the desired concentration.

F4. Coated granules

| | a) | b) | c) |
|---|---|---|---|
| a compound of Tables 1–16 | 0.1% | 5% | 15% |
| highly dispersed silicic acid | 0.9% | 2% | 2% |
| inorganic carrier (diameter 0.1–1 mm) such as $CaCO_3$ or $SiO_2$ | 99.0% | 93% | 83% |

The active ingredient is dissolved in methylene chloride, the solution is sprayed onto the carrier, and the solvent is subsequently evaporated off in vacuo.

F5. Coated granules

| | a) | b) | c) |
|---|---|---|---|
| a compound of Tables 1–16 | 0.1% | 5% | 15% |
| polyethylene glycol mol. wt. 200 | 1.0% | 2% | 3% |
| highly dispersed silicic acid | 0.9% | 1% | 2% |
| inorganic carrier (diameter 0.1–1 mm) such as $CaCO_3$ or $SiO_2$ | 98.0% | 92% | 80% |

The finely ground active ingredient is uniformly applied, in a mixer, to the kaolin moistened with polyethylene glycol. Non-dusty coated granules are obtained in this manner.

F6. Extruder granules

| | a) | b) | c) | d) |
|---|---|---|---|---|
| a compound of Tables 1–16 | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

F7. Dusts

| | a) | b) | c) |
|---|---|---|---|
| a compound of Tables 1–16 | 0.1% | 1% | 5% |
| talcum | 39.9% | 49% | 35% |
| kaolin | 60.0% | 50% | 60% |

Ready-for-use dusts are obtained by mixing the active ingredient with the carriers and grinding the mixture in a suitable mill.

F8. Suspension concentrates

| | a) | b) | c) | d) |
|---|---|---|---|---|
| a compound of Tables 1–16 | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

BIOLOGICAL EXAMPLES

Example B1
Preemergence herbicidal action

Monocotyledonous and dicotyledonous test plants are sown in plastic pots containing standard soil and, immediately after sowing, are sprayed with an aqueous suspension of the test compounds, prepared from a 25% wettable powder formulation (Formulation example F3 b)), corresponding to a rate of application of 2 kg of active ingredient/hectare (500 l of water/ha). The test plants are then cultivated in a greenhouse under optimum conditions. After 3 weeks, the test is evaluated in accordance with a scale of nine ratings (1=total damage, 9=no action). Ratings of 1 to 4 (especially 1 to 3) indicate good to very good herbicidal action.

Test plants: Avena, Lolium, Setaria, Sinapis, Solanum, Stellaria

The compounds of Tables 1 to 16 exhibit pronounced herbicidal action in this test Examples of the good herbicidal action are listed in Table B 1.

TABLE B1

| | | Preemergence action | | | | | |
|---|---|---|---|---|---|---|---|
| Comp. No. | Conc. [kg ai/ha] | Test plants: Avena | Lo-lium | Seta-ria | Sina-pis | Sola-num | Stel-laria |
| 1.005 | 2 | 1 | 2 | 1 | 1 | 1 | 1 |
| 1.008 | 2 | 2 | 1 | 1 | 1 | 1 | 1 |
| 1.075 | 2 | 3 | 1 | 1 | 1 | 1 | 3 |

The same results are obtained when the compounds of formula I are formulated in accordance with Examples F1, F2 and F4 to F8.

Example B2
Post-emergence herbicidal action (contact herbicide)

Monocotyledonous and dicotyledonous test plants are raised in a greenhouse in plastic pots containing standard soil and in the 4- to 6-leaf stage are sprayed with an aqueous suspension of the test compounds of formula I, prepared from a 25% wettable powder formulation (Formulation example F3 b)), corresponding to a rate of application of 2 kg of active ingredient/hectare (500 l of water/ha). The test plants are then grown on in the greenhouse under optimum conditions. After about 18 days the test is evaluated in accordance with a scale of nine ratings (1=total damage, 9=no action). Ratings of 1 to 4 (especially 1 to 3) indicate good to very good herbicidal action.

Test plants: Avena, Lolium, Setaria, Sinapis, Solanum, Stellaria

The compounds of formula I according to the examples in Tables 1 to 16 exhibit good herbicidal action in this test also.

Examples of the good herbicidal activity of compounds of formula I are shown in Table B2.

TABLE B2

| | | Post-emergence action | | | | | |
|---|---|---|---|---|---|---|---|
| Comp. No. | Conc. [kg ai/ha] | Test plants: Avena | Lo-lium | Seta-ria | Sina-pis | Sola-num | Stel-laria |
| 1.005 | 2 | 1 | 1 | 1 | 1 | 1 | 1 |
| 1.008 | 2 | 1 | 1 | 1 | 1 | 1 | 1 |
| 1.075 | 2 | 2 | 1 | 1 | 1 | 1 | 1 |

The same results are obtained when the compounds of formula I are formulated in accordance with Examples F1, F2 and F4 to F8.

What is claimed is:

1. A thiadiazabicyclodecane of formula I

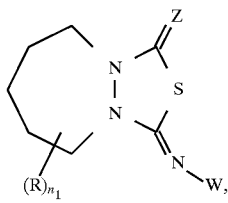
(I)

wherein

Z is oxygen or sulfur;

R is $C_1$–$C_6$alkyl, $C_3$–$C_6$cycloalkyl, $C_1$–$C_6$haloalkyl, $C_3$–$C_6$alkenyl, $C_3$–$C_6$alkynyl, $C_3$–$C_6$haloalkenyl, $C_3$–$C_6$haloalkynyl, phenyl that is unsubstituted or substituted by $C_1$–$C_4$alkyl, $C_1$–$C_4$alkoxy, $C_1$–$C_4$haloalkyl or by halogen, or is benzyl that is unsubstituted or substituted by $C_1$–$C_4$alkyl, $C_1$–$C_4$alkoxy, $C_1$–$C_4$haloalkyl or by halogen, it being possible for the unsubstituted or substituted phenyl and benzyl groups each to occur only once;

W is a group of formula $W_1$ to $W_{10}$

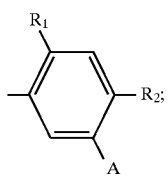
($W_1$)

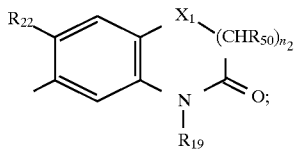
($W_2$)

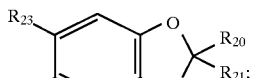
($W_3$)

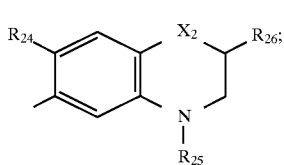
($W_4$)

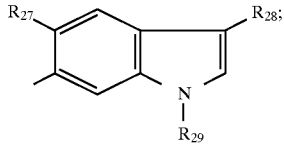
($W_5$)

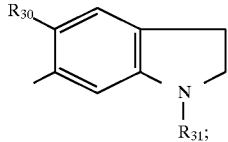
($W_6$)

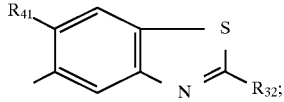
($W_7$)

-continued

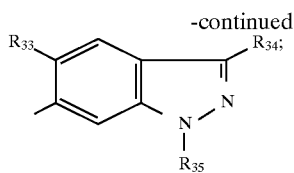
(W₈)

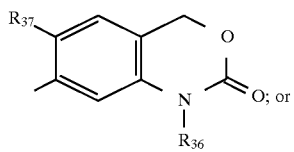
(W₉)

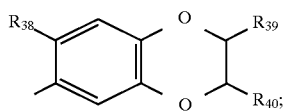
(W₁₀)

R₁, R₂₂, R₂₃, R₂₄, R₂₇, R₃₀, R₃₃, R₃₇, R₃₈ and R₄₁ are each independently of the others hydrogen or halogen;

R₂ is cyano, nitro, halogen, $C_1$–$C_4$alkyl, $C_1$–$C_4$haloalkoxy or $C_1$–$C_4$haloalkyl;

A is hydrogen, cyano, nitro, —COR₃, —X₃P₄,

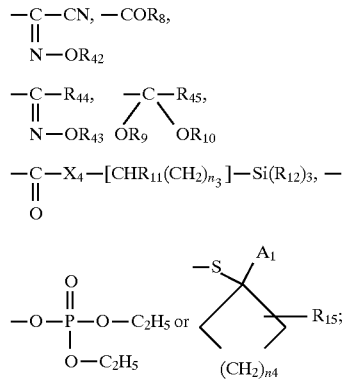

A₁ is cyano or —COR₁₆;

R₃ is halogen, —X₄R₅, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_3$- or $C_4$-alkenylamino, diallylamino, —N-pyrrolidino, —N-piperidino, —N-morpholino, —N-thiomorpholino, —N-piperazino, —O—N=C(CH₃)—CH₃ or —O—CH₂—CH₂—O—N=C(CH₃)—CH₃;

R₄, R₄₂ and R₄₃ are hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, $C_1$–$C_8$haloalkyl, $C_2$–$C_8$alkenyl, $C_2$–$C_8$haloalkenyl, $C_3$–$C_8$alkynyl, $C_3$–$C_7$cycloalkyl, oxetan-3-yl, halo-$C_3$–$C_7$cycloalkyl, $C_1$–$C_8$alkylcarbonyl, alkylcarbonyl, $C_3$–$C_7$cycloalkylcarbonyl, benzoyl that is unsubstituted or is substituted at the phenyl ring by up to three identical or different substituents selected from halogen, $C_1$–$C_4$alkyl, $C_1$–$C_4$haloalkyl, $C_1$–$C_4$haloalkoxy and $C_1$–$C_4$alkoxy; $C_1$–$C_4$alkyl substituted by cyano, nitro, carboxy, $C_1$–$C_8$alkylthio-$C_1$–$C_8$alkoxycarbonyl, phenyl, halophenyl, $C_1$–$C_4$alkylphenyl, $C_1$–$C_4$alkoxyphenyl, $C_1$–$C_4$haloalkylphenyl, $C_1$–$C_4$haloalkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkenyloxycarbonyl, $C_1$–$C_8$allylthiocarbonyl, $C_3$–$C_8$alkenylthiocarbonyl, $C_3$–$C_8$alkynylthiocarbonyl, carbamoyl, $C_1$–$C_4$alkylaminocarbonyl, di-$C_1$–$C_4$alkylaminocarbonyl; phenylaminocarbonyl that is unsubstituted or substituted at the phenyl by up to three identical or different substituents selected from halogen, $C_1$–$C_4$alkyl, $C_1$–$C_4$haloalkyl, $C_1$–$C_4$haloalkoxy and $C_1$–$C_4$alkoxy or by one substituent selected from cyano and nitro; dioxolan-2-yl that is unsubstituted or substituted by one or two $C_1$–$C_4$alkyl radicals; or dioxanyl that is unsubstituted or substituted by one or two $C_1$–$C_4$alkyl radicals;

R₅ is hydrogen, $C_1$–$C_{10}$akyl, $C_1$–$C_4$alkoxy-$C_1$–$C_4$alkyl, $C_2$–$C_8$haloalkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, $C_3$–$C_8$haloalkenyl, $C_3$–$C_8$alkynyl, $C_3$–$C_7$cycloalkyl, oxetan-3-yl, $C_3$–$C_7$cycloalkyl-$C_1$–$C_4$alkyl, halo-$C_3$–$C_7$cycloalkyl, or is benzyl that is unsubstituted or substituted at the phenyl ring by up to three identical or different substituents selected from halogen, $C_1$–$C_4$alkyl, $C_1$–$C_4$haloalkyl, $C_1$–$C_4$haloalkoxy and $C_1$–$C_4$alkoxy; an alkali metal, alkaline earth metal or ammonium ion; or is a group —[CHR₆(CH₂)ₙ₅]-COOR₇;

R₂₀ and R₂₁ are each independently of the other hydrogen, $C_1$–$C_4$alkyl or fluorine;

R₆, R₂₆, R₂₈, R₃₂, R₃₄, R₃₉, R₄₀, R₄₆, R₄₇, R₄₉, R₅₀ and R₅₁ are each independently of the others hydrogen or $C_1$–$C_4$alkyl;

R₇ and R₄₈ are each independently of the other hydrogen, $C_1$–$C_6$alkyl, $C_3$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

R₈ is hydrogen or $C_1$–$C_4$alkyl;

R₄₄ and R₄₅ are each independently of the other hydrogen, $C_1$–$C_4$alkyl, $C_1$–$C_4$haloalkyl or $C_1$–$C_4$alkoxy-$C_1$–$C_4$alkyl;

R₉ and R₁₀ are each independently of the other $C_1$–$C_4$alkyl, $C_2$–$C_4$haloalkyl or $C_2$–$C_8$alkoxyalkyl; or R₉ and R₁₀ together are an ethano, a propano or a cyclohexane-1,2-diyl bridge, it being possible for those groups to be either unsubstituted or substituted by one or two radicals from the group $C_1$–$C_4$alkyl, $C_1$–$C_4$haloalkyl and $C_1$–$C_4$hydroxyalkyl;

R₁₁ is hydrogen, $C_1$–$C_5$alkyl or $C_3$–$C_7$alkenyl;

R₁₂ is $C_1$–$C_8$alkyl;

R₁₃ is hydrogen, $C_1$–$C_5$alkyl, benzyl, $C_1$–$C_4$haloalkyl, $C_3$–$C_8$alkenyl or $C_3$–$C_8$alkynyl;

R₁₄ is $C_1$–$C_6$alkyl, $C_1$–$C_5$haloalkyl or di-$C_1$–$C_4$alkylamino;

R₁₅ is hydrogen, fluorine, chlorine, bromine, $C_1$–$C_4$alkyl or trifluoromethyl;

R₁₆ is chlorine, —X₅—R₁₇, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_3$–$C_4$alkenylamino, diallylamino, —N-pyrrolidino, —N-piperidino, —N-morpholino, —N-thiomorpholino, —N-piperazino, or is a group —O—N=C(CH₃)—CH₃, —O—CH₂—CH₂—O—N=C(CH₃)—CH₃ or —N(OR₄₆)—R₆;

R₁₇ is hydrogen, $C_1$–$C_{10}$alkyl, $C_1$–$C_4$alkoxy-$C_1$–$C_4$alkyl, $C_2$–$C_8$haloalkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, $C_3$–$C_8$haloalkenyl, $C_3$–$C_8$alkynyl, $C_3$–$C_7$cycloalkyl, $C_3$–$C_7$cycloalkyl-$C_1$–$C_4$alkyl, halo- $C_3$–$C_7$cycloalkyl, or is benzyl that is unsubstituted or substituted at the phenyl ring by up to three identical or different substituents selected from halogen, $C_1$–$C_4$alkyl, $C_1$–$C_4$haloalkyl, $C_1$–$C_4$haloalkoxy and $C_1$–$C_4$alkoxy; an alkali metal, alkaline earth metal or ammonium ion, or is a group —[$CHR_{47}$—$(CH_2)_m$]—$COOR_{48}$ or —[$CHR_{49}$—$(CH_2)_t$—$Si(R_{18})_3$];

m is 0,1,2,3 or 4;

t is 0,1,2,3 or 4;

$R_{18}$ is $C_1$–$C_4$alkyl;

$R_{19}$ is hydrogen, $C_1$–$C_6$alkyl, $C_2$–$C_4$alkenyl or $C_2$–$C_6$alkynyl; halo-substituted $C_1$–$C_6$alkyl, $C_2$–$C_4$alkenyl or $C_3$–$C_6$alkynyl; $C_1$–$C_4$alkoxy-$C_1$–$C_4$alkyl, $C_1$–$C_4$alkoxy-$C_1$–$C_2$alkoxy-$C_1$–$C_2$alkyl, 1-phenylpropen-3-yl, cyano- or $C_3$–$C_6$cycloalkyl-substituted $C_1$–$C_6$alkyl; carboxy-$C_1$–$C_4$alkyl, $C_1$–$C_6$alkoxycarbonyl-$C_1$–$C_4$alkyl, $C_2$–$C_6$haloalkoxycarbonyl-$C_1$–$C_4$alkyl, $C_1$–$C_4$alkoxy-$C_1$–$C_2$alkoxycarbonyl-$C_1$–$C_4$alkyl, $C_1$–$C_6$alkoxycarbonyl-$C_1$–$C_2$alkoxycarbonyl-$C_1$–$C_4$alkyl, $C_3$–$C_6$cycloalkyl-$C_1$–$C_2$alkoxycarbonyl-$C_1$–$C_4$alkyl, $C_1$–$C_5$alkylaminocarbonyl-$C_1$–$C_4$alkyl, di-$C_1$–$C_4$alkylamino-$C_1$–$C_4$alkyl, di-$C_1$–$C_5$alkylaminocarbonyl-$C_1$–$C_4$alkyl, $C_3$–$C_6$cycloalkyl, $C_1$–$C_4$alkylthio-$C_1$–$C_4$alkyl, benzyl or halo-substituted benzyl, $C_1$–$C_4$alkylsulfonyl, $C_3$–$C_6$alkenyloxy-$C_1$–$C_4$alkyl, $C_1$–$C_4$alkoxycarbonyl, $C_1$–$C_8$alkylcarbonyl,

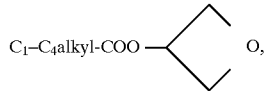

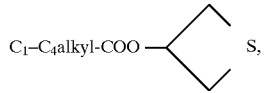

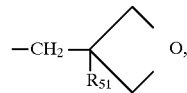

$C_1$–$C_4$alkylthiocarbonyl-$C_1$–$C_4$alkyl, or is a group —[$CHR_{47}$—$(CH_2)_m$]$COX_6$—$CHR_{47}$—$(CH_2)_m$—$COOR_{48}$;

$R_{25}$, $R_{29}$, $R_{31}$, $R_{35}$ and $R_{36}$ are each independently of the others hydrogen, $C_1$–$C_4$alkyl, $C_1$–$C_6$haloalkyl, $C_3$–$C_8$alkenyl, $C_3$–$C_8$haloalkenyl, $C_3$–$C_8$alkynyl, $C_1$–$C_4$alkoxy-$C_1$–$C_8$alkyl, cyano-$C_1$–$C_4$alkyl, $C_1$–$C_8$alkoxycarbonyl-$C_1$–$C_4$alkyl, $C_3$–$C_7$cycloalkyl, $C_3$–$C_7$cycloalkyl-$C_1$–$C_4$alkyl, benzyl, $C_1$–$C_4$alkyl substituted by —N-morpholino, —N-thiomorpholino or by —N-piperazino, di-$C_1$–$C_4$alkylamino-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_1$–$C_4$alkoxycarbonyl or $C_1$–$C_4$alkylcarbonyl;

$X_1$, $X_2$, $X_3$, $X_4$, $X_5$ and $X_6$ are each independently of the others oxygen or sulfur; and $n_1$, $n_2$, $n_3$, $n_4$ and $n_5$ are each independently of the others 0, 1, 2, 3 or 4;

or a salt, complex or stereoisomer thereof.

2. A compound according to claim 1, wherein Z is oxygen.

3. A compound according to claim 1 of formula Ia

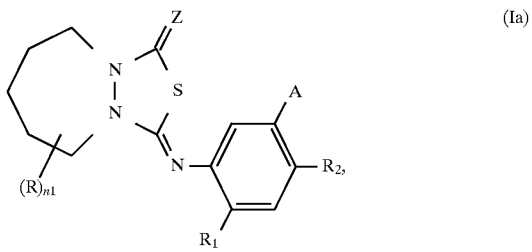

wherein Z, A, R, $R_1$, $R_2$ and $n_1$ are as defined in claim 1.

4. A compound according to claim 3, wherein A is —$X_3R_4$, —$COR_8$, —$COR_3$,

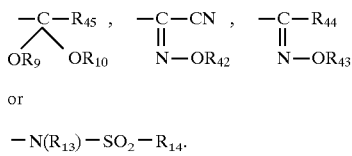

or

—$N(R_{13})$—$SO_2$—$R_{14}$.

5. A compound according to claim 4, wherein $X_3$ is sulfur and $R_4$ is $C_1$–$C_4$alkyl substituted by $C_1$–$C_6$alkoxycarbonyl.

6. A compound according to claim 3, wherein $R_1$ and $R_2$ are halogen.

7. A compound according to claim 6, wherein $R_1$ is fluorine and $R_2$ is chlorine.

8. A compound according to claim 1 of formula Ib

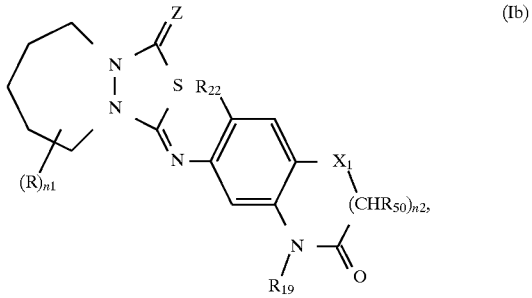

wherein Z, R, $R_{19}$, $R_{22}$, $X_1$, $R_{50}$, $n_1$ and $n_2$ are as defined in claim 1.

9. A compound according to claim 8, wherein $R_{19}$ is $C_1$–$C_4$alkyl, $C_3$- or $C_4$-alkenyl, $C_3$- or $C_4$-haloalkenyl, $C_3$–$C_6$alkynyl, $C_1$–$C_4$alkoxy-$C_1$–$C_4$alkyl, cyano-$C_1$–$C_4$alkyl, $C_1$–$C_6$alkoxycarbonyl-$C_1$–$C_4$alkyl, $C_3$–$C_6$cycloalkyl, $C_3$–$C_6$cycloalkyl-$C_1$–$C_4$alkyl, benzyl, di-$C_1$–$C_4$alkylamino-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_1$–$C_4$alkoxycarbonyl or $C_1$–$C_4$alkylcarbonyl.

10. A compound according to claim 9, wherein

Z is oxygen;

$R_{19}$ is $C_1$–$C_3$alkyl, $C_1$–$C_3$alkoxycarbonyl-$C_1$- or -$C_2$-alkyl or $C_3$- or $C_4$-alkynyl;

$R_{22}$ is hydrogen or fluorine;

$R_{50}$ is hydrogen; and $n_2$ is 0 or 1.

11. A compound according to claim 1, wherein $n_1$ is 0 or 1.

12. A compound according to claim 11, wherein $n_1$ is 0.

13. A compound according to claim 1 selected from the group 10-(4-chloro-2-fluoro-5-isopropoxycarbonyl-phenylimino)-9-thia-1,7-diazabicyclo[3.5.0]-decan-8-one; and 10-(4-chloro-2-fluoro-5-methoxycarbonyl-phenylimino)-9-thia-1,7-diazabicyclo[3.5.0]-decan-8-one.

14. A process for the preparation of a compound of formula I

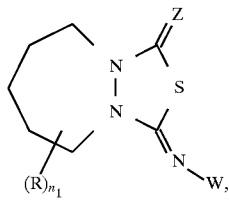   (I)

wherein Z, W, R and $n_1$ are as defined for formula I in claim 1, which comprises converting an isothiocyanate of formula II

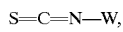   (II)

wherein W is as defined for formula I in claim 1, with a compound of formula III

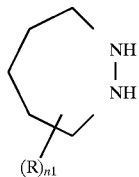   (III)

wherein R and $n_1$ are as defined, into a compound of formula IV

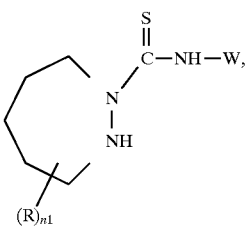   (IV)

which is then reacted, where appropriate in the presence of a base, with a compound of formula V

   (V)

wherein Z is oxygen or sulfur.

15. A herbicidal composition which comprises a herbicidally effective amount of a compound of formula I or a salt thereof according to claim 1 and an inert carrier.

16. A herbicidal composition according to claim 15, which comprises from 0.1 to 95 percent by weight of at least one active ingredient of formula I.

17. A method of controlling undesired plant growth, which comprises treating the crop plants to be protected against weeds and grasses and/or treating the undesired weeds and grasses or the locus of said crops weeds or grasses: (1) with a herbicidally effective amount of a compound of formula I or a salt thereof according to claim 1 or (2) with a herbicidal composition comprising a herbicidally effective amount of a compound of formula I or a salt thereof and an inert carrier.

18. A method according to claim 17 which comprises applying a compound of formula I in an amount of from 0.001 to 2 kg per hectare.

19. A method according to claim 17 for the selective pre- or post-emergence control of weeds and grasses in crops of useful plants.

* * * * *